US010890577B2

(12) United States Patent
Turgeon et al.

(10) Patent No.: US 10,890,577 B2
(45) Date of Patent: Jan. 12, 2021

(54) TREATMENT METHODS HAVING REDUCED DRUG-RELATED TOXICITY AND METHODS OF IDENTIFYING THE LIKELIHOOD OF PATIENT HARM FROM PRESCRIBED MEDICATIONS

(71) Applicant: TABULA RASA HEALTHCARE, INC., Moorestown, NJ (US)

(72) Inventors: Jacques Turgeon, Philadelphia, PA (US); Lauren E. Steffen, Levittown, PA (US); Gabriel Badea, Prevost (CA); Veronique Michaud, Orlando, FL (US)

(73) Assignee: TABULA RASA HEALTHCARE, INC., Moorestown, NJ (US)

(*) Notice: Subject to any disclaimer, the term of this patent is extended or adjusted under 35 U.S.C. 154(b) by 0 days.

(21) Appl. No.: 16/302,824

(22) PCT Filed: May 19, 2017

(86) PCT No.: PCT/US2017/033539
§ 371 (c)(1),
(2) Date: Nov. 19, 2018

(87) PCT Pub. No.: WO2017/213825
PCT Pub. Date: Dec. 14, 2017

(65) Prior Publication Data
US 2019/0293631 A1    Sep. 26, 2019

Related U.S. Application Data

(60) Provisional application No. 62/338,704, filed on May 19, 2016.

(51) Int. Cl.
| A61K 31/445 | (2006.01) |
| G01N 33/50 | (2006.01) |
| A61P 9/06 | (2006.01) |
| A61B 5/046 | (2006.01) |
| A61B 5/0464 | (2006.01) |
| A61K 49/00 | (2006.01) |
| G01N 33/68 | (2006.01) |
| A61K 45/06 | (2006.01) |

(52) U.S. Cl.
CPC ......... G01N 33/5014 (2013.01); A61B 5/046 (2013.01); A61B 5/0464 (2013.01); A61K 31/445 (2013.01); A61K 49/0004 (2013.01); A61P 9/06 (2018.01); G01N 33/6893 (2013.01); A61K 45/06 (2013.01); G01N 2800/326 (2013.01); G01N 2800/50 (2013.01)

(58) Field of Classification Search
CPC .............................. A61K 31/00; A61K 31/445
See application file for complete search history.

(56) References Cited

U.S. PATENT DOCUMENTS

| 2007/0031817 | A1* | 2/2007 | Yan | G01N 33/5088 435/4 |
| 2009/0326023 | A1 | 12/2009 | Neubert et al. | |

FOREIGN PATENT DOCUMENTS

| WO | 96/28537 A1 | 9/1996 |
| WO | 2006121943 A2 | 11/2006 |
| WO | WO2006121943 | * 11/2006 |
| WO | 2012/167212 A2 | 12/2012 |

OTHER PUBLICATIONS

International Search Report and Written Opinion of the International Searching Authority, dated Sep. 21, 2017, for International Application No. PCT/US2017/033539.
Supplementary Partial European Search Report dated Nov. 15, 2019 issued in connection with EP Application No. 17810690.2, 12 pages.
Lawrence Helson et al, "Liposome mitigation of curcumin inhibition of cardiac potassium delayed-rectifier current", Journal of Receptor, Ligand and Channel Research, Nov. 1, 2012, pp. 1-8.
Jerome Thireau et al., "New drugs vs. old concepts: A fresh look at antiarrhythmics", Pharmacology and Therapeutics, vol. 132, No. 2, Mar. 21, 2011, pp. 125-145.
Peter J. Schwartz et al., "Predicting the Unpredictable Drug-Induced QT Prolongation and Torsades de Pointes", Journal of the American College of Cardiology, vol. 67, No. 13, Mar. 28, 2016, pp. 1639-1650.
Extended European Search Report dated Feb. 28, 2020 issued in connection with EP Application No. 17810690.2, 12 pages.
Gowda Ramesh M et al.: "Torsade de pointes: the clinical considerations", International Journal of Cardiology, Elsevier, Amsterdam, NL, vol. 96, No. 1, Jul. 1, 2004, pp. 1-6, XP002413352.
Chiang C-E et al.: "The Long QT Syndromes: Genetic Basis and Clinical Implications", Journal of the American College of Cardiology, Elsevier, New York, NY, US, vol. 36, No. 1, Jul. 1, 2000, pp. 1-12, XP001145655.

* cited by examiner

*Primary Examiner* — Rei Tsang Shiao
(74) *Attorney, Agent, or Firm* — Morgan, Lewis & Bockius LLP

(57) ABSTRACT

Methods of determining whether specific drugs or patients carry an increased risk of causing or developing, respectively, long QT syndrome or Torsades de Pointes and methods of treating such patients.

9 Claims, 21 Drawing Sheets

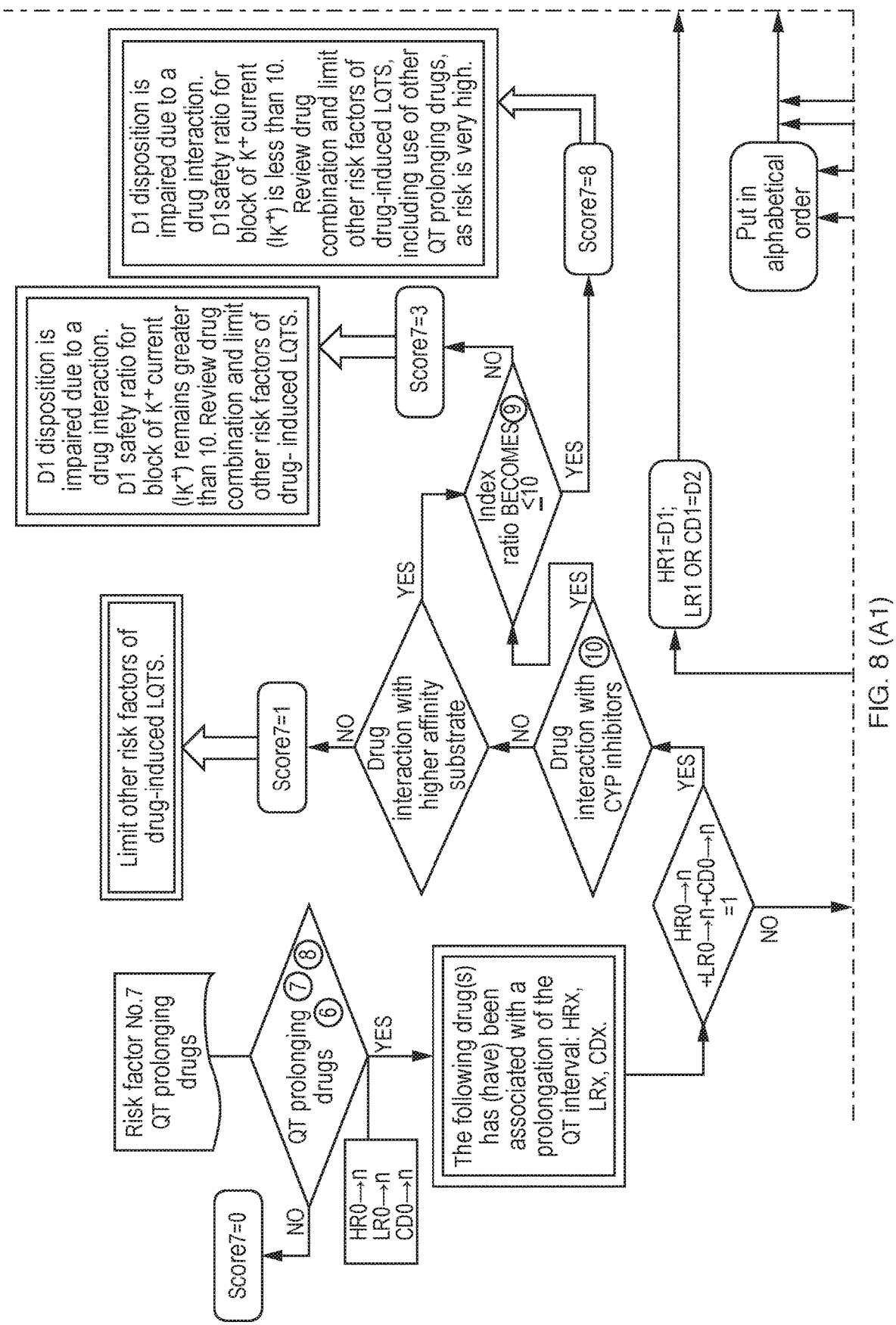
FIG. 8 (A1)

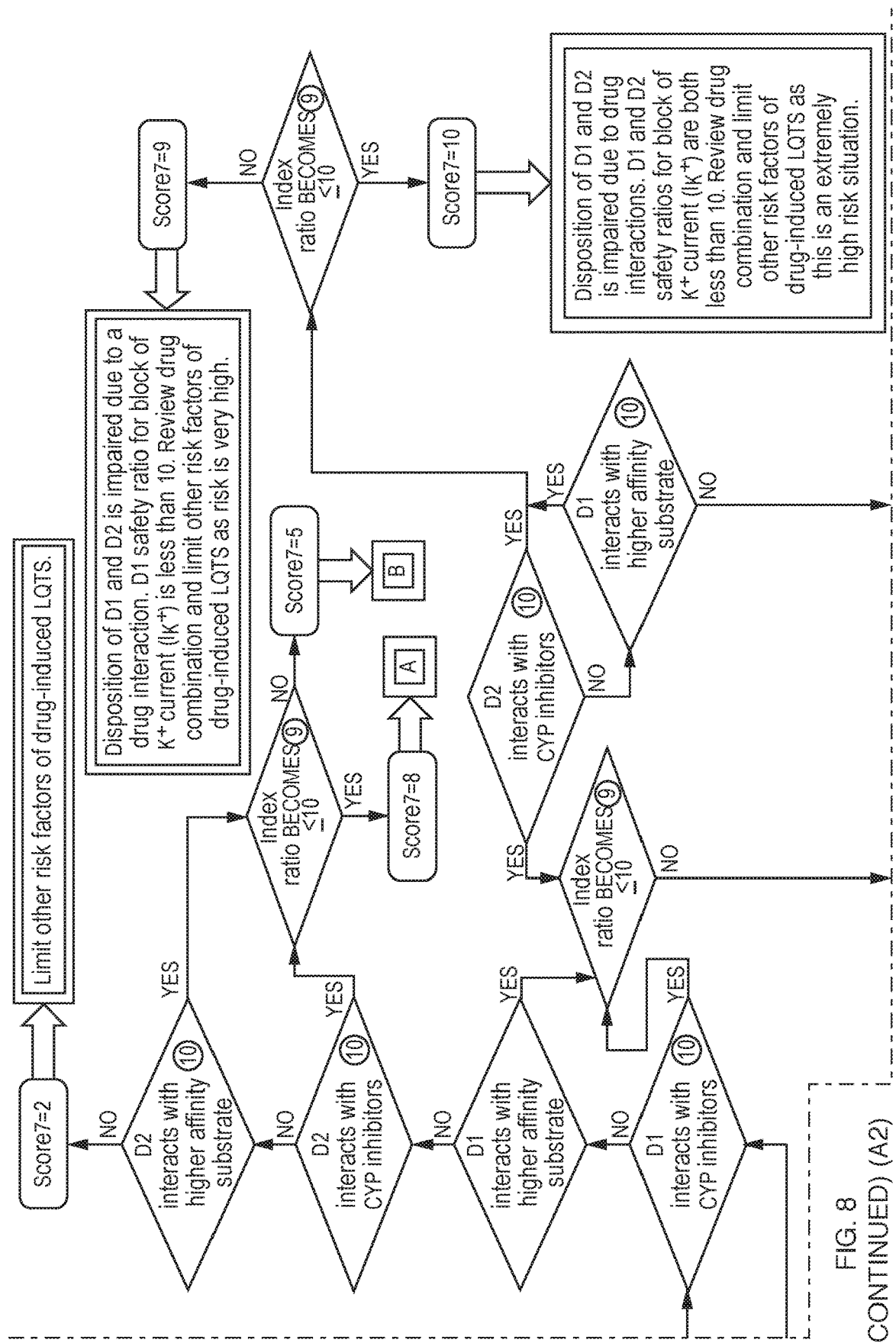
FIG. 8 (CONTINUED) (A2)

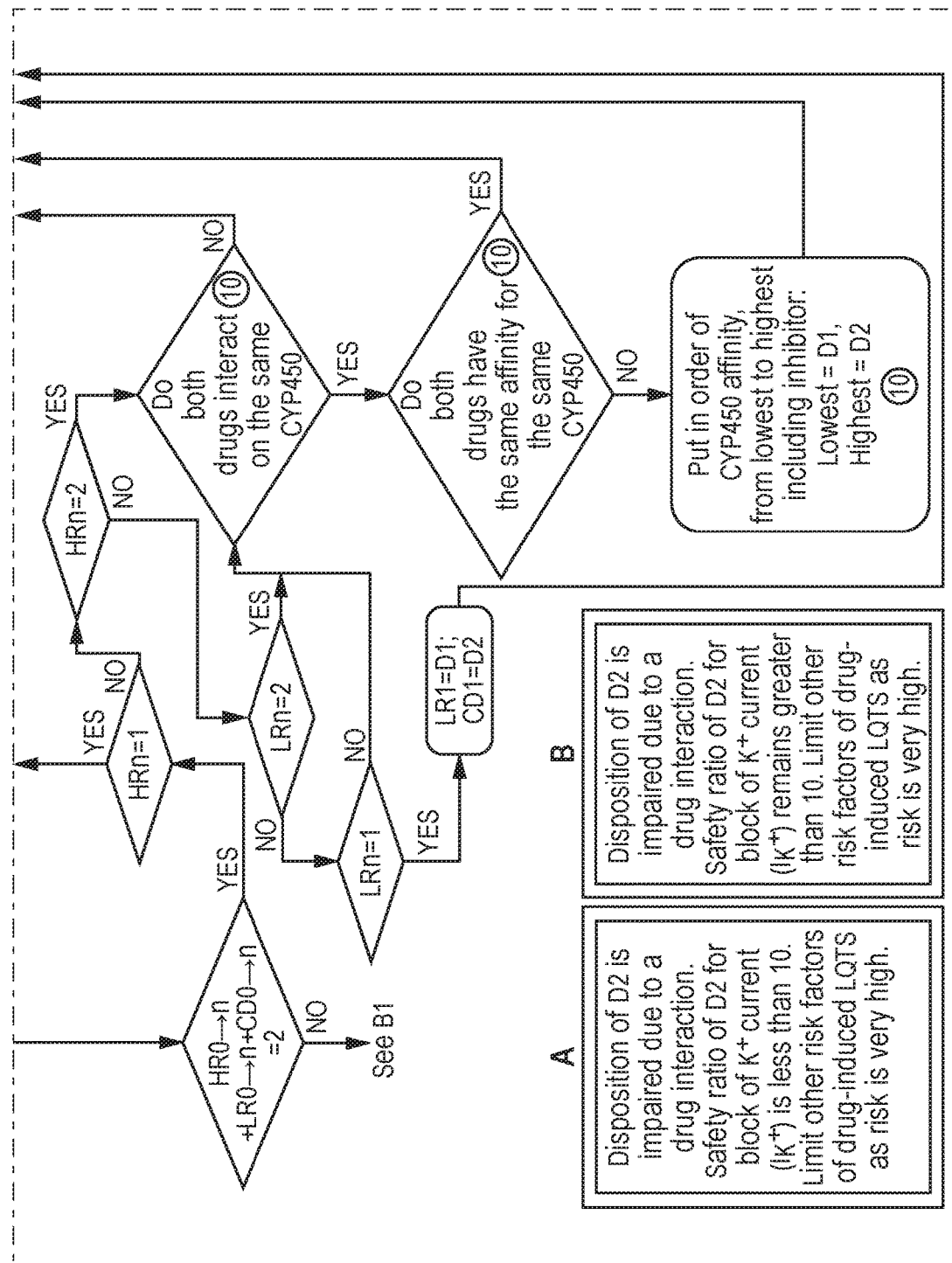
FIG. 8 (CONTINUED) (A3)

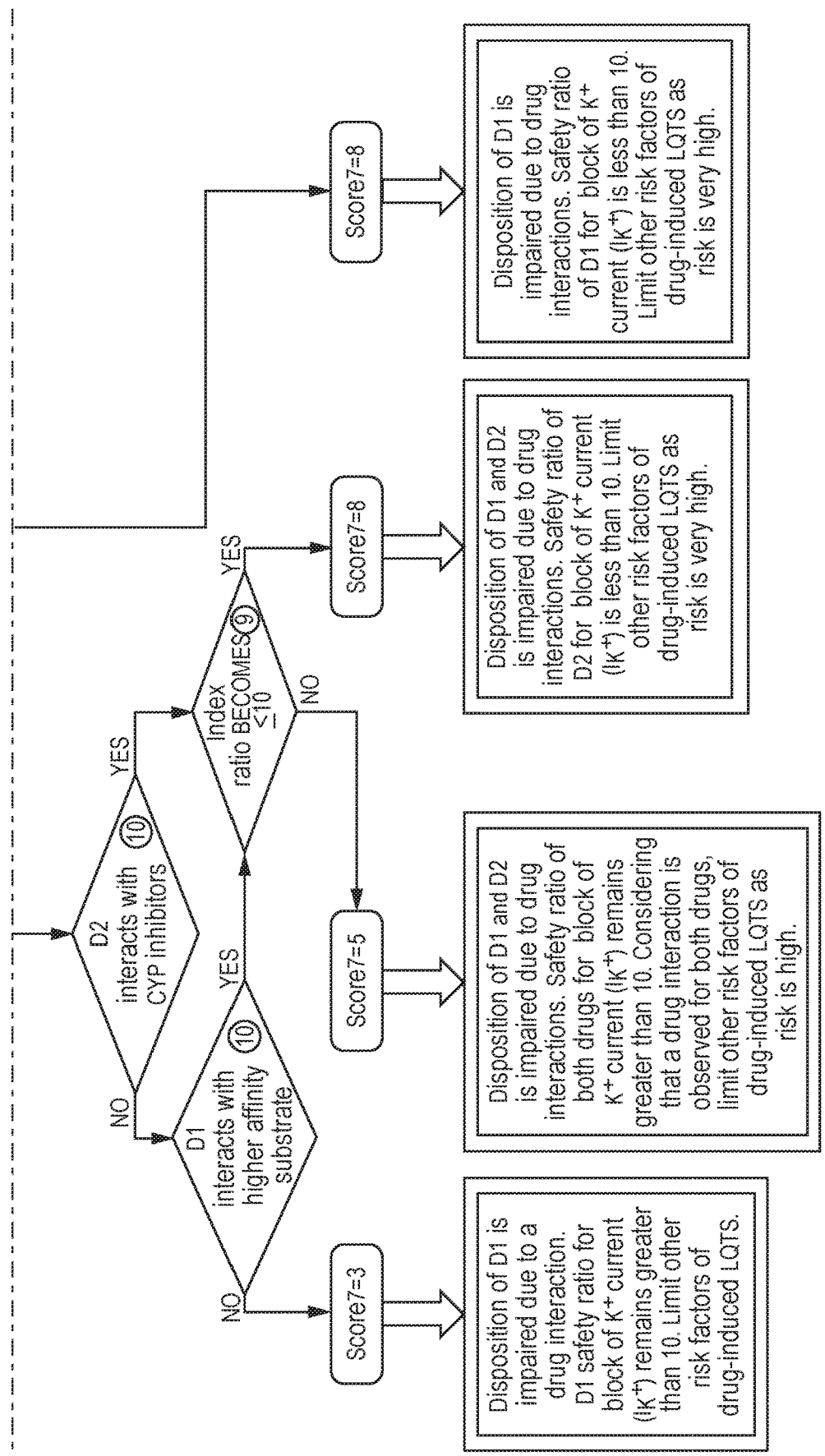
FIG. 8 (CONTINUED)(A4)

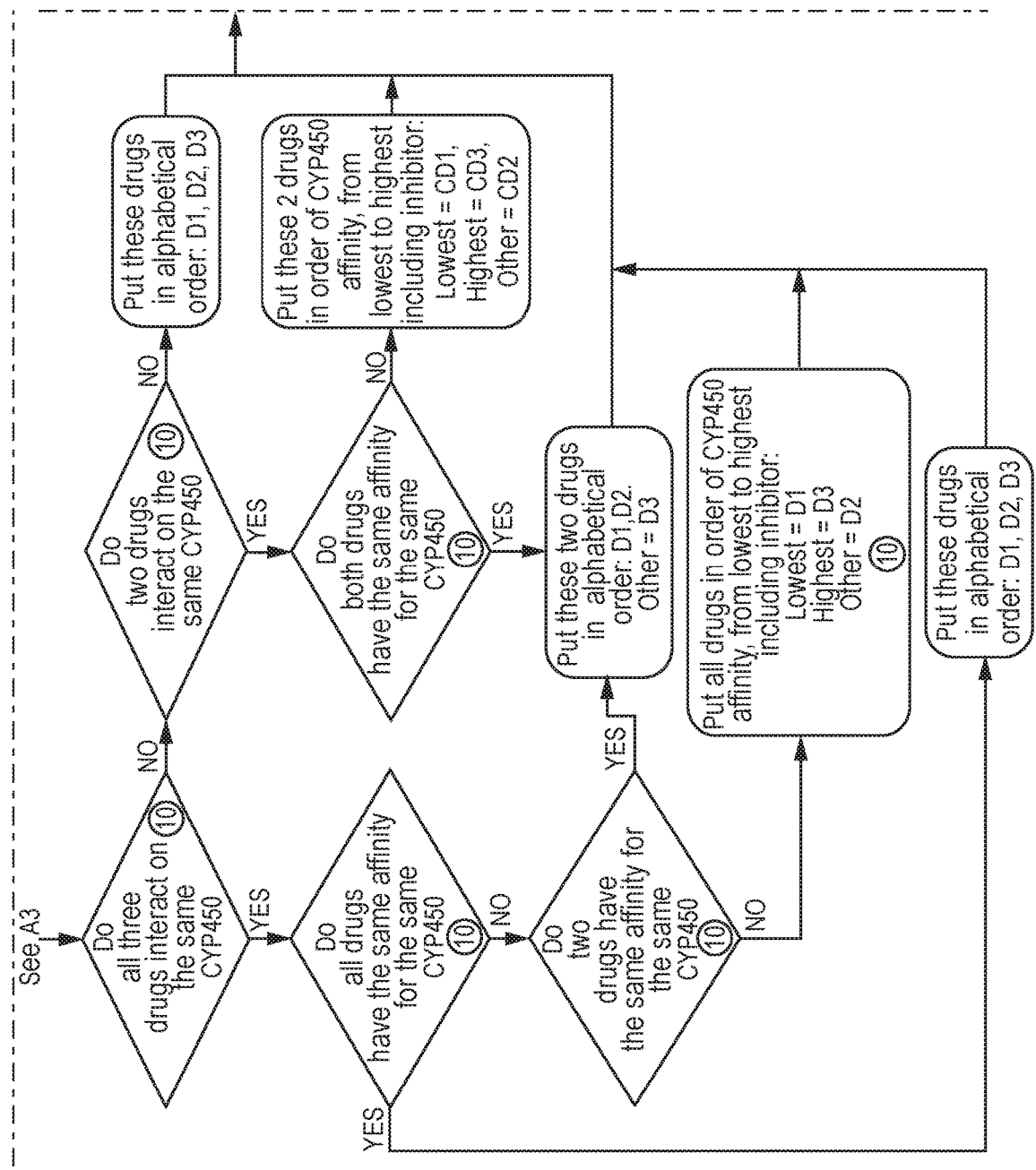
FIG. 8 (CONTINUED) (B1)

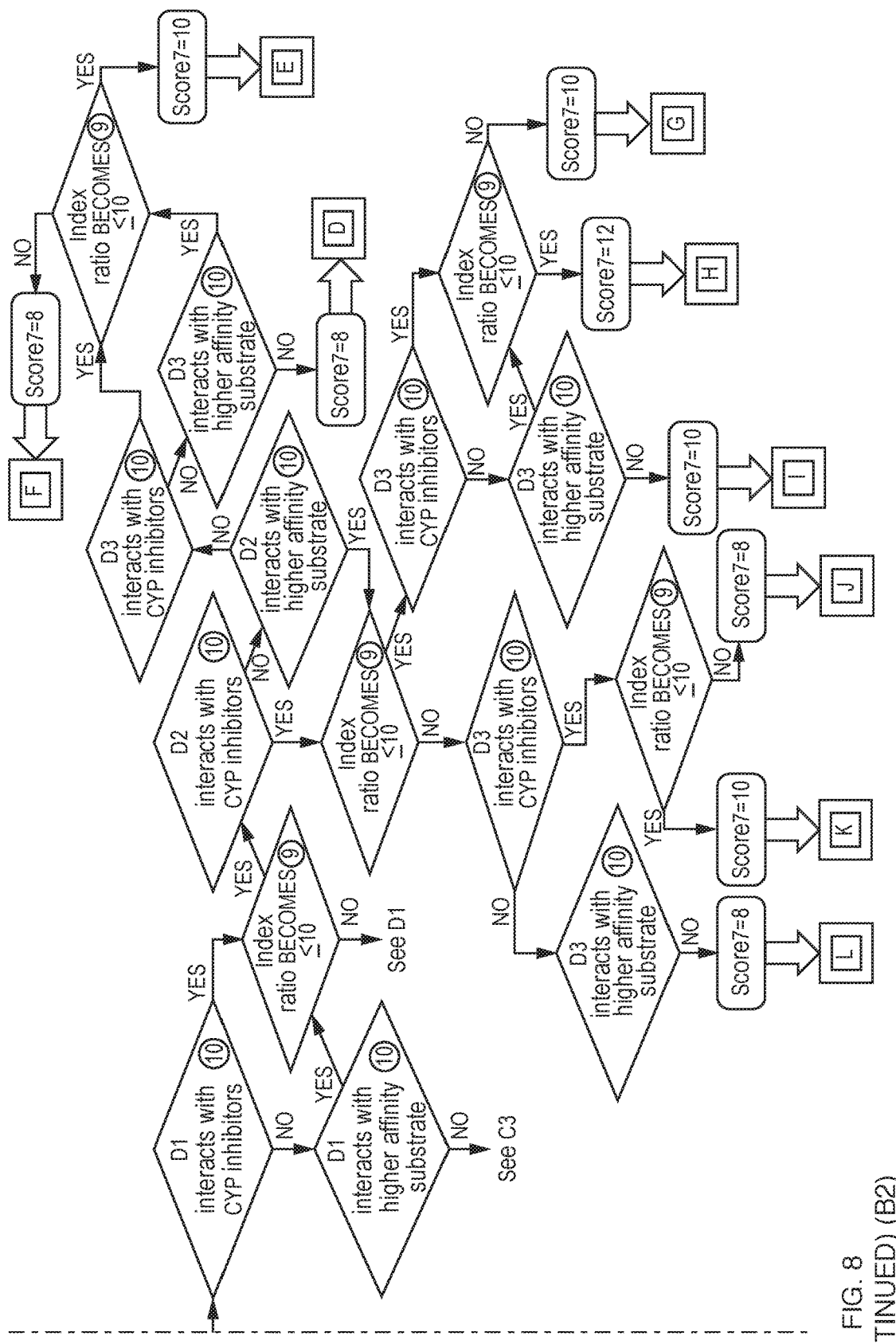
FIG. 8 (CONTINUED) (B2)

C
Limit other risk factors of drug-induced LQTS.

D
Disposition of D1 is impaired due to drug interactions. D1 and D3 safety ratios for block of K+ current (Ik+) is less than 10. Limit other risk factors of drug-induced LQTS as risk is very high.

E
Disposition of D2 and D3 is impaired due to drug interactions. D1 and D3 safety ratios for block of K+ current (Ik+) are both less than 10. Review drug combination and limit other risk factors of drug-induced LQTS as this is an extremely high risk situation.

F
Disposition of D2 and of D3 is impaired due to drug interactions. D1 safety ratio for block of K+ current (Ik+) are less than 10. Review drug combination and limit other risk factors of drug-induced LQTS as this is a very high risk situation.

G
Disposition of D1, D2 and D3 is impaired due to drug interactions. D1 and D2 safety ratios for block of K+ current (Ik+) are less than 10. Review drug combination and limit other risk factors of drug-induced LQTS as this is an extremely high risk situation.

H
Disposition of D1, D2 and D3 is impaired due to drug interactions. D1, D2, and D3 safety ratios for block of K+ current (Ik+) are less than 10. Review drug combination and limit other risk factors of drug-induced LQTS as this is an extremely high risk situation.

I
Disposition of D1 and D2 is impaired due to drug interactions. D1 and D2 safety ratio for block of K+ current (Ik+) are less than 10. Review drug combination and limit other risk factors of drug-induced LQTS as this is an extremely high risk situation.

J
Disposition of D1 is impaired due to a drug interaction. D1 safety ratio for block of K+ current (Ik+) remains greater than 10. Limit other risk factors of drug-induced LQTS.

FIG. 8 (CONTINUED) (C1)

K Disposition of D1 and D3 is impaired due to drug interactions. D3 safety ratio for block of K+ current (IK+) is less than 10. Limit other risk factors of drug-induced LQTS as risk is very high.

L Disposition of D1 and D2 is impaired due to drug interactions. D1 safety ratio for block of K+ current (IK+) is less than 10. Limit other risk factors of drug-induced LQTS as risk is high.

M Disposition of D1, D2, and D3 is impaired due to drug interactions. D2 safety ratio for block of K+ current (IK+) is less than 10. Limit other risk factors of drug-induced LQTS as risk is very high.

N Disposition of D1, D2, and D3 is impaired due to drug interactions. D2 and D3 safety ratios for block of K+ current (IK+) are less than 10. Limit other risk factors of drug-induced LQTS as risk is extremely high.

O Disposition of D1 and D2 is impaired due to drug interactions. D2 safety ratio for block of K+ current (IK+) is less than 10. Limit other risk factors of drug-induced LQTS as risk is very high.

P Disposition of D1, D2, and D3 is impaired due to drug interactions. Their safety ratio for block of K+ current (IK+) remains greater than 10. Limit other risk factors of drug-induced LQTS as risk is high.

Q Disposition of D1, D2, and D3 is impaired due to drug interactions. D3 safety ratio for block of K+ current (IK+) is less than 10. Limit other risk factors of drug-induced LQTS as risk is very high.

R Disposition of D1 and D2 is impaired due to drug interactions. Safety ratios of D1, D2, and D3 for block of K+ current (IK+) remain greater than 10. Limit other risk factors of drug-induced LQTS.

S Disposition of D3 is impaired due to drug interactions. D3 safety ratio for block of K+ current (IK+) is less than 10. Limit other risk factors of drug-induced LQTS as risk is very high.

FIG. 8
(CONTINUED) (C2)

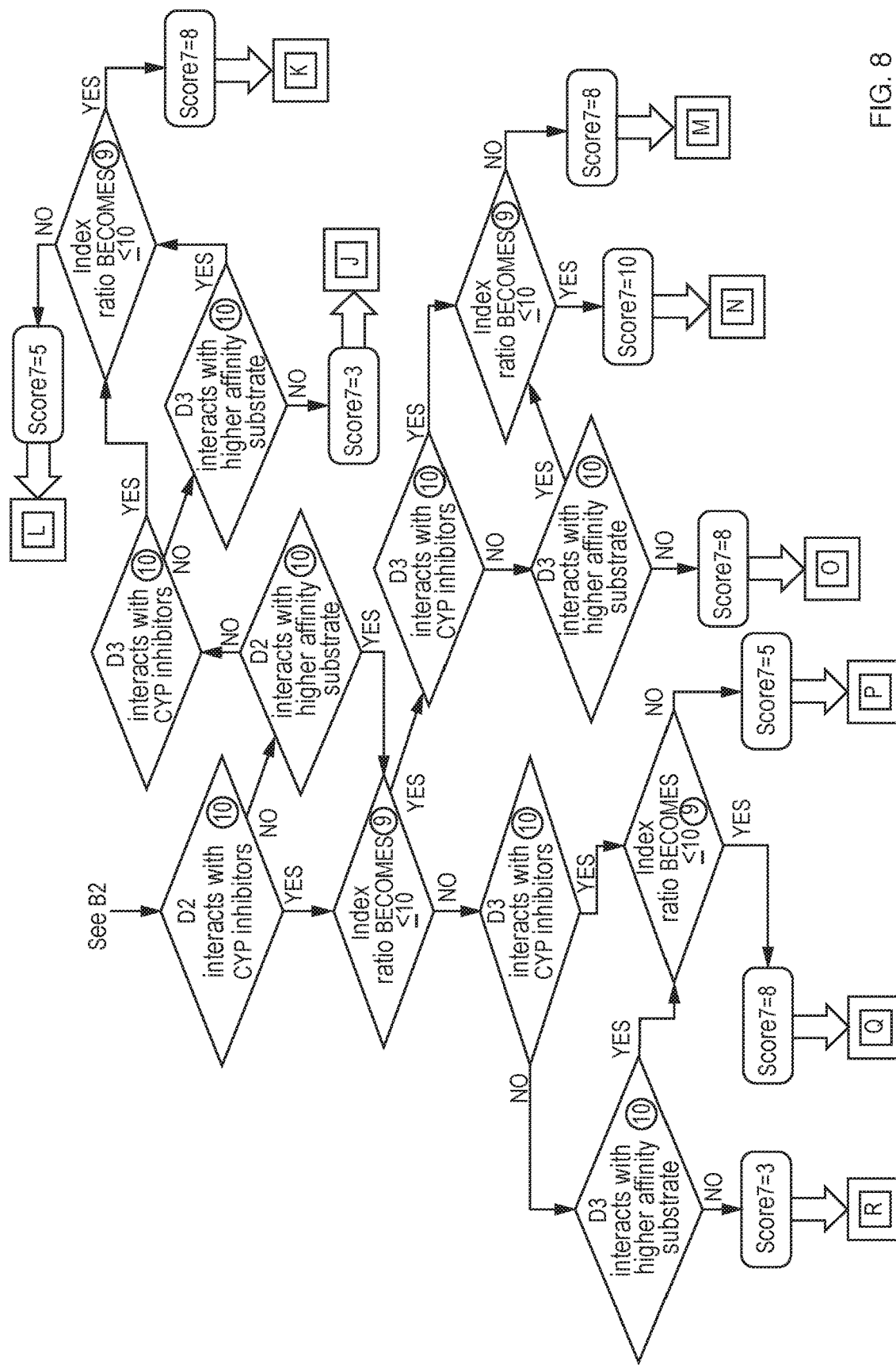
FIG. 8 (CONTINUED) (C3)

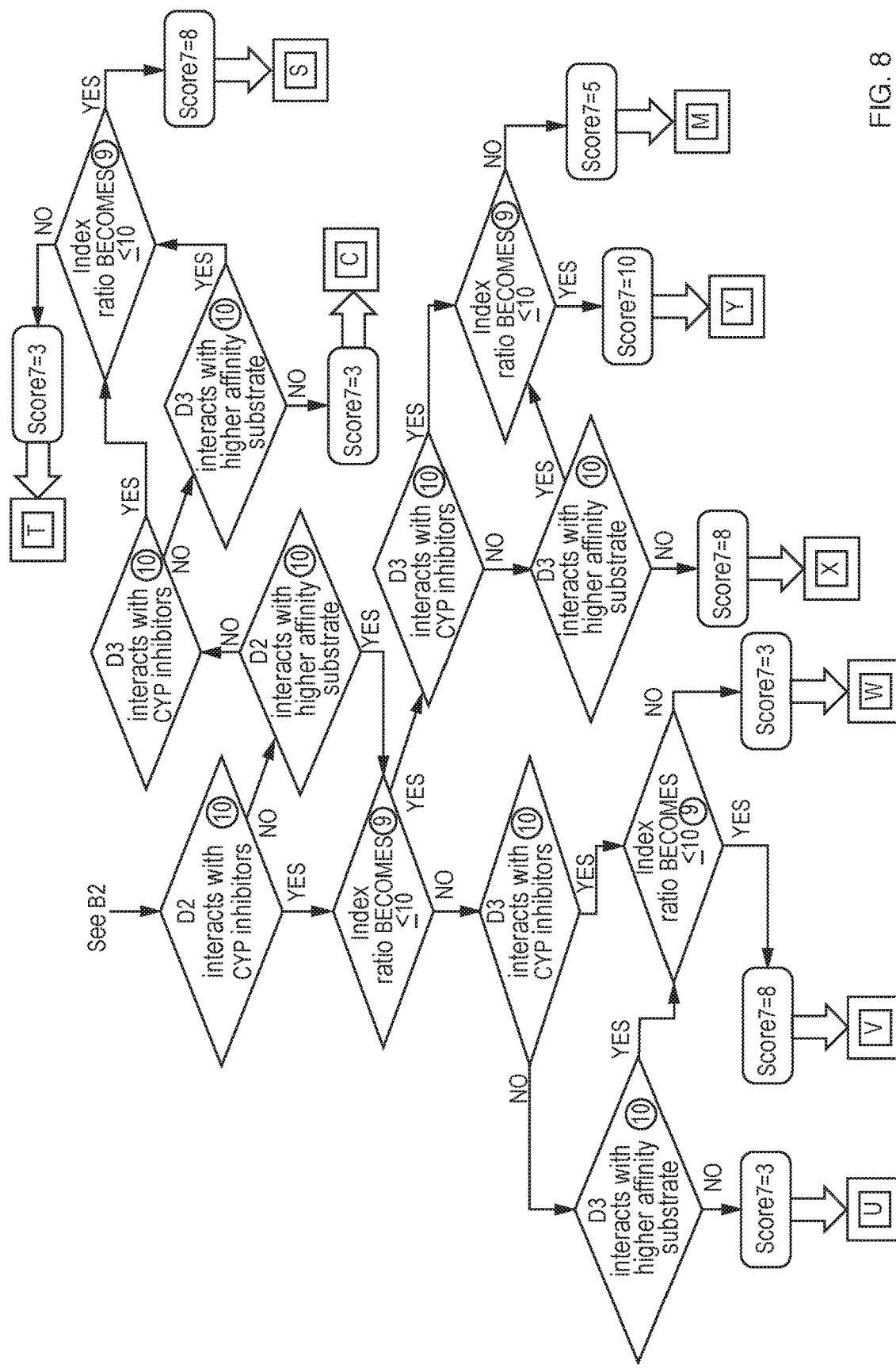
FIG. 8 (CONTINUED) (D1)

T

Disposition of D3 is impaired due to a drug interaction. D3 safety ratio for block of K+ current (Ik+) is greater than 10. Limit other risk factors of drug-induced LQTS.

U

Disposition of D2 is impaired due to a drug interaction. D2 safety ratios for block of K+ current (Ik+) remains greater than 10. Limit other risk factors of drug-induced LQTS as risk is very high.

V

Disposition of D2 and D3 is impaired due to drug interactions. D3 safety ratio for block of K+ current (Ik+) is less than 10. Limit other risk factors of drug-induced LQTS as risk is very high.

W

Disposition of D2 and D3 is impaired due to drug interactions. D2 and D3 safety ratios for block of K+ current (Ik+) remain greater than 10. Limit other risk factors of drug-induced LQTS.

X

Disposition of D2 is impaired due to a drug interaction. D2 safety ratio for block of K+ current (Ik+) is less than 10. Limit other risk factors of drug-induced LQTS as risk is very high.

Y

Disposition of D2 and D3 is impaired due to drug interactions. D2 and D3 safety ratios for block of K+ current (Ik+) are less than 10. Limit other risk factors of drug-induced LQTS as risk is extremely high.

Z

Disposition of D2 and D3 is impaired due to drug interactions. D2 safety ratio for block of K+ current (Ik+) is less than 10. Limit other risk factors of drug-induced LQTS as risk is very high.

FIG. 8 (CONTINUED) (D2)

| Gender: | Female ▸ | Regular Sinus: | No ▸ | Heart Rate: | ▸ |
| Syncope: | Unknown ▸ | Pacemaker: | Unknown ▸ | Sick Sinus: | Unknown ▸ |
| Magnesium (meq/L): | | Potassium (meq/L): | 3.1 | Atrial Fib: | Yes |
| QTc: | 560 | Age: | | MPC: | 30 |
| Substance: | Ciprofloxacin | | ▸ | Add Substance | Clear |

| Substance name | Dose | Unit | Remove |
|---|---|---|---|
| Sotalol | 0 | mg ▸ | Delete |
| Ciprofloxacin | 0 | mg ▸ | Delete |

Submit for analysis

FIG. 10

TREATMENT METHODS HAVING REDUCED DRUG-RELATED TOXICITY AND METHODS OF IDENTIFYING THE LIKELIHOOD OF PATIENT HARM FROM PRESCRIBED MEDICATIONS

CROSS-REFERENCE TO RELATED APPLICATIONS

This application is a U.S. national stage of International Application No. PCT/US2017/033539, filed May 19, 2017, which claims the benefit of priority of U.S. Provisional Application No. 62/338,704, filed May 19, 2016, the entire contents of each are incorporated herein by reference.

FIELD OF THE INVENTION

The invention described herein relates in general to the development and use of (1) a drug-specific index computed from distinct drug characteristics; and (2) a patient-specific score computed from predefined values of selected risk factors of drug related toxicity. In some embodiments, these two aspects of the invention contribute to reduce the likelihood of patient harm arising from prescribed medications.

BACKGROUND OF THE INVENTION

While medications are a necessary intervention for the prevention and treatment of disease, disability, and death, they may also cause problems on a broad scale. One particular side-effect that may be associated with certain drugs is a perturbation of the heart's capability to regain its basic membrane potential after a heartbeat. Such condition is associated with a prolongation of the QT interval on the surface electrocardiogram (ECG) and is generally described as drug-induced long QT Syndrome (LQTS). Prolongation of the QT interval may predispose patients to syncope events and a particular polymorphic ventricular tachycardia described as Torsades de Pointes.

Many medications have been implicated in the initiation of drug-induced LQTS. In the past 20 years, drug-induced QT prolongation and hence, Torsades de Points, has led to withdrawal from the market of at least 6 medications and publications of several black box warnings in the United States. The Food and Drug Administration now requires study of this phenomenon prior to market approval.

Accordingly, there is a need in the field for methods of treatment that allow for the avoidance of drug-induced LQTS and methods of identifying drugs or drug combinations that may result in drug-induced LQTS.

SUMMARY OF THE INVENTION

The inventions described herein provide a comprehensive approach that includes a number of factors that may influence a medication's likelihood of causing drug-induced LQTS and/or Torsades de Pointes. In some embodiments, the Long QT-JT Index takes into account the scenario where a medication has the greatest chance of causing Torsades de Pointes—when a medication is the most "risky." The following factors may be considered specific to each medication:

1. $IC_{50}$ for block of $I_{Kr}$;
2. $IC_{50}$ for block of $I_{Ks}$;
3. $IC_{50}$ for block of Nav1.5 (sodium) current;
4. $IC_{50}$ for block of Cav1.2 (calcium) current;
5. Inhibition of hERG trafficking;
6. Cmax of the drug at a test Dose;
7. Maximum daily dose of the drug according to labelling;
8. Protein binding of the drug; and/or
9. Drug-drug interaction coefficient (DDIC).

In some embodiments, the Drug-drug interaction coefficient takes into account the pharmacokinetics of the medication—whether it has a high extraction ratio (low bioavailability) or low extraction ratio (high bioavailability), relative enzymatic pathways involved in the clearance of the drug.

While the medication-specific risk index will be helpful when scrutinizing a single medication, the reality is that patients take many medications and have individual risk factors that may predispose or protect them from QT prolongation and Torsades de Pointes.

In some embodiments, a patient-specific Long QT-JT Score is provided that is dynamic based on the patient's current conditions and concomitant medications. The risk factors are included based on the evidence described herein, and may be assigned points as follows:

| Risk Factor | Description | Points Range |
|---|---|---|
| 1 | Male or female gender, also includes age for males | 0-0.5 |
| 2 | Heart Rhythm: sinus rhythm, Atrial Fibrillation, Sick Sinus Syndrome, Pause, Heart Rate, Beta-blocker usage | 0-1 |
| 3 | Hypokalemia (K < 3.5 mEq/L); use of triamterene | 0-1 |
| 4 | Hypomagnesemia (Mg < 1.5 mEq/L) | 0-1 |
| 5 | Diuretics | 0-1 |
| 6 | Antiarrhythmics: Class IA, Class IC, Class III; amiodarone | 0-9 |
| 7 | QT-prolonging drugs and drug interactions | 0-12 |
| 8 | QTc interval (Cut-offs: <450, <475, <500, <550, 550 + msec) | 0-10 |

The scoring mechanisms described herein have been validated against literature cases of known Torsades de Pointes. More than 50 cases of documented Torsades de Pointes have been identified due to medication use and/or medication interactions and their risk score has been calculated based on the methods described herein. In such cases, the risk scores are generally above 10.

In some embodiments, the foregoing and other objects and advantages of the invention are obtained by using a method for estimating risk of drug-related problems either due to drug characteristics or a patient's overall drug regimen and conditions.

In an embodiment, the invention includes a method for determining whether a compound is associated with an increased risk of long QT syndrome or Torsades de Pointes by determining a drug-specific index. In some embodiments, the method may include the step of measuring a first index variable, which may include determining one or more of (1) an $IC_{50}$ value for block of one or more of $I_{Kr}$ and $I_{Ks}$, (2) a Cmax of the compound at a test dose, (3) a daily dose amount of the compound, (4) a protein binding value for the compound at a target protein, and (5) a drug-drug interaction coefficient (DDIC) for the compound. In some embodiments, the method may include the step of measuring a second index variable, which may include determining one or more of (1) an $IC_{50}$ value for block of CaV1.2 current, and (2) the $IC_{50}$ value for block of one or more of $I_{Kr}$ and $I_{Ks}$. In some embodiments, the method may include the step of measuring a third index variable, which may include determining one or more of (1) an $IC_{50}$ value for block of NaV1.5 current, and (2) the $IC_{50}$ value for block of one or more of $I_{Kr}$ and $I_{Ks}$. In some embodiments, the method may include the step of measuring a fourth index variable, which may include determining a fourth index variable, which may include determining a qualitative value for the compound's inhibition of hERG trafficking. In some embodiments, the method may include the step of combining the first, second, third, and/or fourth index variables to provide the drug-specific index, which is indicative of an increased risk of long QT syndrome or Torsades de Pointes. In some embodiments, a drug-specific index of less than 15 is indicative of an increased risk of long QT syndrome or Torsades de Pointes. In some embodiments, a drug-specific index of greater than 15 is not indicative of an increased risk of long QT syndrome or Torsades de Pointes.

In an embodiment, the invention includes a method for determining whether a patient undergoing treatment with a compound has an increased risk of long QT syndrome or Torsades de Pointes by determining a patient-specific score. In some embodiments, the method may include the steps of: (1) determining a risk variable based on the patient's gender and age; (2) measuring the patient's heart rhythm including detecting one or more of a sinus rhythm, atrial fibrillation, sick sinus syndrome, pause, and heart rate; (3) detecting a potassium level in the patient; (4) detecting a magnesium level in the patient; (5) detecting the presence of one or more diuretics or antiarrhythmics in the patient; (6) measuring a drug-specific index for one or drug therapeutics in the patient's treatment regimen; and (7) measuring the patient's QT interval. In some embodiments, the method may further include the step of calculating the patient-specific score based on quantitative results collected from the steps of: (1) determining a risk variable based on the patient's gender and age; (2) measuring the patient's heart rhythm including detecting one or more of a sinus rhythm, atrial fibrillation, sick sinus syndrome, pause, and heart rate; (3) detecting a potassium level in the patient; (4) detecting a magnesium level in the patient; (5) detecting the presence of one or more diuretics or antiarrhythmics in the patient; (6) measuring a drug-specific index for one or drug therapeutics in the patient's treatment regimen; and (7) measuring the patient's QT interval. In some embodiments, a patient-specific score of greater than 10 is indicative of an increased risk of long QT syndrome or Torsades de Pointes. In some embodiments, a patient specific score of less than 10 is not indicative of an increased risk of long QT syndrome or Torsades de Pointes.

In an embodiment, the invention includes a method for determining whether a patient undergoing treatment with a compound has an increased risk of long QT syndrome or Torsades de Pointes by determining a patient specific score, which may include the steps of: (1) determining a risk variable having a value based on the patient's gender and/or age; (2) determining a risk variable having a value based on the patient's heart rhythm, which may include determining one or more of the patient's sinus rhythm, atrial fibrillation, sick sinus syndrome, pause, heart rate, and beta-blocker usage; (3) determining a risk variable having a value based on the patient having hypokalemia (i.e., a potassium level of less than 3.5 mEq/L) and/or the patient's use of triamterene; (4) determining a risk variable having a value based on the patient having hypomagnesemia (i.e., a magnesium level of less than 1.5 mEq/L); (5) determining a risk variable having a value based on the patient's use of diuretics; (6) determining a risk variable having a value based on the patient's use of an antiarrhythmic, such as, for example, a Class IA, Class IC, or Class III antiarrhythmic, or amiodarone; (7) determining a risk variable having a value based on the patient's use of QT-prolonging drugs and/or the presence of drug-drug interactions, which may include the measurement of a drug-specific index and/or a drug-drug interaction coefficient (DDIC) for the QT-prolonging drugs used by the patient; and (8) determining a risk variable having a value based on the patient's QTc interval. In some embodiments, the method may further include the step of calculating the patient-specific score based on an analysis of the risk variables determined in the steps of: (1) determining a risk variable having a value based on the patient's gender and/or age; (2) determining a risk variable having a value based on the patient's heart rhythm, which may include determining one or more of the patient's sinus rhythm, atrial fibrillation, sick sinus syndrome, pause, heart rate, and beta-blocker usage; (3) determining a risk variable having a value based on the patient having hypokalemia (i.e., a potassium level of less than 3.5 mEq/L) and/or the patient's use of triamterene; (4) determining a risk variable having a value based on the patient having hypomagnesemia (i.e., a magnesium level of less than 1.5 mEq/L); (5) determining a risk variable having a value based on the patient's use of diuretics; (6) determining a risk variable having a value based on the patient's use of an antiarrhythmic, such as, for example, a Class IA, Class IC, or Class III antiarrhythmic, or amiodarone; (7) determining a risk variable having a value based on the patient's use of QT-prolonging drugs and/or the presence of drug-drug interactions, which may include the measurement of a drug-specific index and/or a drug-drug interaction coefficient (DDIC) for the QT-prolonging drugs used by the patient; and (8) determining a risk variable having a value based on the patient's QTc interval. In some embodiments, a patient-specific score of greater than 10 is indicative of an increased risk of long QT syndrome or Torsades de Pointes. In some embodiments, a patient specific score of less than 10 is not indicative of an increased risk of long QT syndrome or Torsades de Pointes.

In an embodiment, the invention includes a method of treating patients having an increased risk of developing long QT syndrome or Torsades de Pointes due to a patient-specific score of greater than 10. In some embodiments, the method may include the administration of a therapeutically effective amount of a compound selected from the group consisting of a potassium salt and a magnesium salt. In some embodiments, the potassium salt may be potassium chloride. In some embodiments, the magnesium salt may be magnesium sulfate.

In an embodiment, the invention includes a method of treating a patient with a compound determined to increase the risk of long QT syndrome or Torsades de Pointes. In some embodiments, the method may include the step of confirming that the patient does not have an increased risk of developing long QT syndrome or Torsades de Pointes due to a patient-specific score of greater than 10. In some embodiments, the method may include the step of administering a pharmaceutical composition to the patient including a therapeutically effective amount of the compound or a pharmaceutically acceptable salt thereof, and a pharmaceutically acceptable carrier. In some embodiments, the compound determined to increase the risk of long QT syndrome or Torsades de Pointes may include one or more of Albuterol, Alfuzosin, Amantadine, Amiodarone, Amitriptyline, Amphetamine, Arsenic trioxide, Astemizole, Atazanavir, Atomoxetine, Azithromycin, Bepridil, Chloral hydrate, Chloroquine, Chlorpromazine, Ciprofloxacin, Cisapride, Citalopram, Clarithromycin, Clomipramine, Clozapine, Cocaine, Desipramine, Dexmethylphenidate, Diphenhydramine, Diphenhydramine, Disopyramide, Dobutamine, Dofetilide, Dolasetron, Domperidone, Dopamine, Doxepin, Dronedarone, Droperidol, Ephedrine, Epinephrine, Erythromycin, Escitalopram, Escitalopram, Famotidine, Felbamate, Fenfluramine, Flecamide, Fluconazole, Fluoxetine, Foscarnet, Fosphenyloin, Galantamine, Gatifloxacin, Gemifloxacin, Granisetron, Halofantrine, Haloperidol, Ibutilide, Imipramine, Indapamide, Isoproterenol, Isoproterenol, Isradipine, Itraconazole, Ketoconazole, Lapatinib, Lapatinib, Levalbuterol, Levofloxacin, Levomethadyl, Lisdexamfetamine, Lithium, Mesoridazine, Metaproterenol, Methadone, Methylphenidate, Midodrine, Moexipril/HCTZ, Moxifloxacin, Nicardipine, Nilotinib, Norepinephrine, Nortriptyline, Octreotide, Ofloxacin, Ondansetron, Oxytocin, Paliperidone, Paroxetine, Pentamidine, Perflutren lipid microspheres, Phentermine, Phenylephrine, Phenylpropanolamine, Pimozide, Probucol, Procainamide, Protriptyline, Pseudoephedrine, Quetiapine, Quinidine, Ranolazine, Risperidone, Ritodrine, Ritonavir, Roxithromycin, Salmeterol, Sertindole, Sertraline, Sibutramine, Solifenacin, Sotalol, Sparfloxacin, Sunitinib, Tacrolimus, Tamoxifen, Telithromycin, Terbutaline, Terfenadine, Thioridazine, Tizanidine, Tolterodine, Trazodone, Trimethoprim-Sulfa, Trimipramine, Vandetanib, Vardenafil, Venlafaxine, Voriconazole, Ziprasidone, and the pharmaceutically acceptable salts thereof.

In an embodiment, the invention may include a method of treating a patient with a compound determined to increase the risk of long QT syndrome or Torsades de Pointes, which may include the step of administering a pharmaceutical composition to the patient including a therapeutically effective amount of the compound or a pharmaceutically acceptable salt thereof, and a pharmaceutically acceptable carrier. In some embodiments, the method may include the step of determining whether the patient has an increased risk of developing long QT syndrome or Torsades de Pointes due a patient-specific score that is indicative of an increased risk of developing long QT syndrome or Torsades de Pointes. In some embodiments, the patient-specific score that is indicative of an increased risk of developing long QT syndrome or Torsades de Pointes is greater than 10. In some embodiments, the method may further include halting treatment of the patient with the pharmaceutical composition. In some embodiments, the method may further include the administration of an additional pharmaceutical composition to the patient that does not include the compound. In some embodiments, the additional pharmaceutical composition includes an additional compound that has a drug-specific index of greater than 15.

In some embodiments, the methods described herein may utilize a non-transitory computer readable medium having program instructions stored in a memory device, the instructions executable by a processor to direct the performance of operations to estimate drug-related or patient-related risk. In some embodiments, the program instructions for determining drug-specific index for a drug or combination of drugs may comprise the steps of:

importing a first data set comprising $IC_{50}$ for block of $I_{Kr}$ and/or $I_{Ks}$, $IC_{50}$ for block of Nav1.5 (sodium) current, $IC_{50}$ for block of Cav1.2 (calcium) current, a qualitative value for inhibition of hERG trafficking, Cmax of the drug at a test dose, daily dose of the drug being used, and/or protein binding of the drug or combination of drugs; and importing a second data set comprising metabolic pathways and extent of metabolism of the drug or combination of drugs as well as the degree of competitive inhibition from other drugs or combinations of drugs in a patient's drug regimen to establish a drug-drug interaction coefficient (DDIC).

In some embodiments, the program instructions for determining a patient-specific score may comprise the steps of:

importing a data set comprising gender, age, heart rhythm—whether sinus rhythm, atrial fibrillation, sick sinus syndrome, pause, heart rate—and beta-blocker usage, hypokalemia, hypomagnesemia, diuretic use, antiarrhythmic use, Long QT-JT Index value of each drug used by this patient, QTc interval, ongoing drugs and drug-drug interactions. In some embodiments, data set forth herein may be processed by eight pre-defined algorithms to calculate patient-specific Long QT-JT Scores.

BRIEF DESCRIPTION OF THE DRAWINGS

The foregoing summary, as well as the following detailed description of the invention, will be better understood when read in conjunction with the appended drawings.

FIG. 8 is a chart illustrating the algorithm used for calculation of risk factor 7.

FIG. 10 is a chart illustrating the input of an example patient's parameters into the Long QT-JT Score.

DETAILED DESCRIPTION OF THE INVENTION

Figure 1:
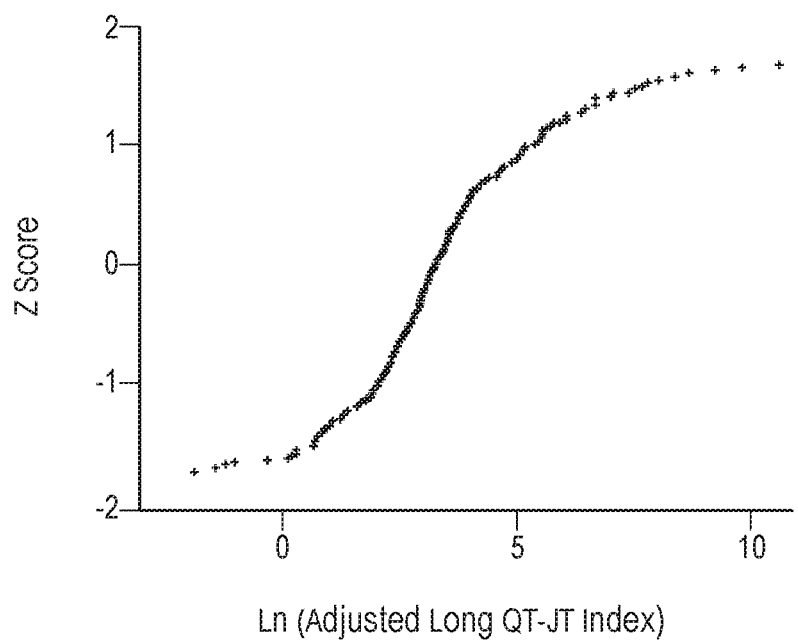
FIG. 1 is a chart illustrating the Z-distribution of Long QT-JT Index for 155 drugs.

Unless defined otherwise, all technical and scientific terms used herein have the same meaning as is commonly understood by one of skill in the art to which this invention belongs. All patents and publications referred to herein are incorporated by reference in their entireties.

Definitions

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "drug-specific index" or "drug-specific LQTS index" or "Long QT-JT Index" are interchangeable and refer to a value determined according to the methods described herein for a drug, which is indicative of the drug's propensity for causing long QT syndrome or Torsades de Pointes. As described herein, a drug-specific index of less than 15 is associated with an increased risk of causing long QT syndrome or Torsades de Pointes. In some embodiments, a drug-specific index of less than about 15 is associated with an increased risk of causing long QT syndrome or Torsades de Pointes.

The terms "patient-specific score" or "patient-specific LQTS score" or "patient-specific Long QT-JT score" are interchangeable and refer to a value determined according to the methods described for a patient, which is indicative of the patient's risk for developing long QT syndrome or Torsades de Pointes. As described herein, a patient-specific score of greater than 10 is associated with an increased risk of developing long QT syndrome or Torsades de Pointes. In some embodiments, a patient-specific score of greater than about 10 is associated with an increased risk of developing long QT syndrome or Torsades de Pointes.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

For the avoidance of doubt, it is intended herein that particular features (for example integers, characteristics, values, uses, diseases, formulae, compounds or groups) described in conjunction with a particular aspect, embodiment or example of the invention are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any disclosed embodiments. The invention extends to any novel one, or novel combination, of the features disclosed in this specification (including any accompanying claims, abstract and drawings), or to any novel one, or any novel combination, of the steps of any method or process so disclosed.

QT Prolongation and Development of Torsades de Pointes Following Long QT Interval The cardiomyocyte plasma membrane is, in principle, impermeable to ion flow. Thus, influx and efflux of ions can occur only following the opening of voltage-gated or agonist-gated ion channels or through the action of ion transporters (pumps). With respect to these channels and transporters underlying the ventricular action potential and, hence, the corresponding surface ECG waves, Phase 4 of the action potential corresponds to ventricular diastole when ventricular myocytes are at their resting potential. At this stage, the concentration of K⁺ is higher inside the cell than outside; and the concentration of Na⁺ and Ca²⁺ are higher outside the cells than inside. Only specific K⁺ channels ($I_{K1}$, $I_{Kach}$, $I_{KATP}$) will show some openings during this phase creating an inward electrical gradient (as positive charges like K⁺ prefer to stay inside the cells, which have a negative potential) and an outward chemical gradient (as K⁺ prefers to exit the intracellular milieu where there is a large concentration of this ion compared to the extracellular cleft).

When extracellular K⁺ concentration is 3.5 mM and intracellular K⁺ is 150 mM, the system comes into equilibrium at a voltage of −80 mV.

Phase 0 of the action potential is characterized by the opening of voltage-gated Na⁺ channels when the plasma membrane reaches −70 mV. Hence, a rapid influx of Na⁺ occurs due to both an inward chemical gradient and an inward electrical gradient. As transmembrane potential reaches −50 mV, voltage-gated Ca²⁺ channels open allowing inward flow of Ca²⁺. On one hand, the increase in intracellular Na⁺ depolarizes the nearby cells (as Na⁺ flows through gap junctions between cardiac myocytes) and assures propagation of the influx. On the other hand, the increase in intracellular Ca²⁺ will trigger calcium release (calcium-induced calcium release) from the sarcoplasmic reticulum and contraction will occur. The depolarization of ventricular cardiac myocytes and the conduction of the influx throughout the ventricles is depicted on the surface ECG by the QRS wave.

This is followed by Phase 1, where there is some outward transient K⁺ current and a decreased inward Na⁺ current; Phase 1 corresponds to an early repolarization phase where some transient K⁺ channels open ($I_{to}$). The presence of $I_{to}$ differentiates between endocardial, epicardial, and M cells.

Phase 2 is considered the plateau phase. During this phase there is roughly equivalent influx of Ca²⁺ via L-type channels in proportion to the efflux of K⁺—this is the systole of the ventricles during which actin and myosin interact.

Phase 3—the recovery phase—involves a decrease in inward Ca²⁺ influx, a recovery of intracellular Ca²⁺ by the sarcoplasmic reticulum, and a significant increase in the efflux of K⁺. Within the K⁺ efflux, there are two main channels to consider. The channel $I_{Kr}$, synonymous with hERG-KCNH2+Mirp1-KCNE2, is responsible for the rapid repolarization, whereas delayed repolarization is attributed to $I_{Ks}$ (KvLQT1−KCNQ1+mink−KCNE1.

Finally, Phase 4 is the cell's return to its resting membrane potential.

There are many factors that can impact a ventricular cell's capacity to repolarize. As discussed above, repolarization of ventricular myocytes primarily occurs in Phase 3 via the efflux of K⁺ through $I_{Kr}$ and $I_{Ks}$ channels. Block of $I_{Kr}$ alone may be associated with significant prolongation of the QTc interval as the major outward current at physiological heart rates. The slow component ($I_{Ks}$) is a reserve current which contributes to repolarization when APD is prolonged due to dysfunctional $I_{Kr}$, or, to the contrary, when heart rate accelerates. Indeed, it is the accumulation of $I_{Ks}$ (which is slow to open but also slow to close) that explains shortening of the APD at faster heart rates. Block of $I_{Ks}$ by itself has little effect on the APD at physiological heart rates, but changes QT the rate adaptation curve.

Inappropriate inactivation of the late Na⁺ current (SNC5A: window current) can also prolong the ventricular action potential duration. Mutations in the various components of $I_{Kr}$, $I_{Ks}$, and $I_{Na}$ have all been associated with the inherited and drug-induced forms of LQTS. If a single repolarization mechanism is disturbed, there may be little to no effect on the QT interval; however, if multiple mechanisms are impaired, there may be clinically significant effects on QTc interval and risk of Torsades de Pointes.

There are varying degrees to which medications can affect the QT interval based on various properties. Studies have been performed to analyze the effect of certain medications on the QT interval length, as well as the relationship between QT interval length, as well as the relationship between QT interval and adverse outcomes, the most significant being sudden cardiac death. Studies have been carried out to examine patients who had previously taken medications in certain categories, which were known to result in a known Torsades de Pointes risk, conditional Torsades de Pointes risk, and possible Torsades de Pointes risk. It has been found that the QTc interval is prolonged by 15 milliseconds when patients are given a drug categorized as "known" Torsades de Pointes risk; whereas, for drugs with "possible" Torsades de Pointes risk; the QTc lengthened by 3 milliseconds.

When certain studies looked at the addition of a 2nd or 3rd QTc prolonging drug to the patient's regimen, it produced no substantial increase in QTc. Without being limited to any one theory, if the 2nd and/or 3rd medication prolongs the QTc interval by the same mechanism, then there is little room for QTc prolongation beyond what the 1st medication caused. The clinical significance of QTc prolongation lies with the risk that Torsades de Pointes can degenerate into ventricular fibrillation, causing sudden cardiac death. This progression is more common with long episodes of Torsades de Pointes, which are also more commonly, but has also been related to QTc interval length.

In relating the QTc interval to Torsades de Pointes, specifically, it has been estimated that each 10 millisecond increase in QTc corresponds to a 5-7% exponential increase in risk for Torsades de Pointes. Another study has demonstrated that 89.5% of drug-induced Torsades de Pointes occurred when QTc was greater than 500 msec. In general, Torsades de Pointes is rare when QTc is <500 ms, accounting for less than 10% of all cases.

Certain studies have shown a relationship between QTc length and mortality, reinforcing the need to take action when a prolonged QTc is identified. Another study indicated that mortality from any cause for patients with QTc of 500 ms or greater is 19% (87 out of 470) compared to 5% for those with QTc less than 500 ms (total 51,434 patients) ($p<0.001$). Specifically, certain studies showed that the QTc interval as a significant predictor of mortality with a hazard ratio of 1.13 (1.12-1.14, $p<0.001$), meaning patients with a prolonged QTc interval are 13% more likely to experience death than those with a normal QTc interval length.

Method of Determining Drug-Specific LQTS Index

In some embodiments, the invention described herein includes methods for determining a drug-specific LQTS index to determine a drug or combination of drugs likelihood of causing drug-induced LQTS or Torsades de Pointes. The Long QT-JT Index described herein takes into account the scenario where a medication has the greatest chance of causing Torsades de Pointes, when a medication may be viewed as risky. In some embodiments, the following factors may be considered specific to each medication under consideration:

1. $IC_{50}$ for block of $I_{Kr}$;
2. $IC_{50}$ for block of $I_{Ks}$;
3. $IC_{50}$ for block of Nav1.5 (sodium) current;
4. $IC_{50}$ for block of Cav1.2 (calcium) current;
5. Inhibition of hERG trafficking;

6. Cmax of the drug at a test dose;
7. Maximum daily dose of the drug according to labelling;
8. Protein binding of the drug; and/or
9. Drug-drug interaction coefficient (DDIC).

As described herein, each of the ion currents may increase or decrease a drug's propensity to cause Torsades de Pointes. The DDIC takes into account the pharmacokinetics of the medication: whether it has a high extraction ratio (low bioavailability) or low extraction ratio (high bioavailability). This is important since changes in concentration will occur with varying magnitudes.

In embodiment, a method for determining a drug's Long QT-JT index is as described herein. In some embodiments, the method may include measuring a drug's:

1. $IC_{50}$ for block of $I_{Kr}$ (in µM);
2. $IC_{50}$ for block of $I_{Ks}$ (in µM);
3. $IC_{50}$ for block of Nav1.5 (sodium) current (in µM);
4. $IC_{50}$ for block of Cav1.2 (calcium) current (in µM);
5. Inhibition of hERG trafficking (true or false);
6. Cmax of the drug at a test dose (in nM);
7. Maximum daily dose of the drug according to labeling (in µmoles);
8. Protein binding of the drug (in percent binding at the listed protein target); and/or
9. Drug-drug interaction coefficient (DDIC) (see below).

Upon measuring the foregoing variables, the Long QT-JT Index may be calculated based on the following equation:

Long QT-JT Index=$K1+K2'+K3'+K4'$, where $$K1 = \frac{(IC_{50} \text{ of } I_{Kr} \text{ or } I_{Ks} \text{ block}) \times 1000}{\left((cmax \text{ Dose Test}) \times \frac{100 - \text{Protein Binding \%}}{100}\right) \times \left(\frac{\text{Daily Dose Administered (}\mu\text{moles)}}{\text{Dose Test (}\mu\text{mole)} \times DDIC}\right)}$$

$$K2 = \frac{IC_{50} \text{ for block of } CaV1.2 \text{ current}}{IC_{50} \text{ for lock of } I_{Kr} \text{ or } I_{Ks}}$$

$$K3 = \frac{IC_{50} \text{ for block of } NaV1.5 \text{ current}}{IC_{50} \text{ for block of } I_{Kr} \text{ or } I_{Ks}}$$

$K4$ = Inhibition of hERG trafficking

With regard to K2, if K2 is less than 1, then K2' is 10. If K2 is between 1 to less than 5, then K2' is 5. If K2 is between 5 and less than 10, then K2' is 2.

With regard to K3, if K3 is less than 1, then K3' is 10. If K3 is between 1 to less than 5, then K3' is 5. If K3 is between 5 and less than 10, then K3' is 2.

With regard to K4, if K4 is true and the drug is an inhibitor of hERG trafficking, then K4' is −5. If K4 is false and the drug is not an inhibitor of hERG trafficking, then K4' is 0. Therefore, if K4 is true, then subtract 5 from the sum of K1, K2', and K3'.

In some embodiments, drugs having a Long QT-JT Index of less than 15 are likely to carry a high risk of Torsades de Pointes (i.e., (K1+K2'+K3'+K4')<15).

In some embodiments, the Drug-Drug Interaction Coefficient (DDIC) takes into account the pharmacokinetics of a particular drug or medication: whether it has a high extraction ratio (low bioavailability) or low extraction ratio (high bioavailability). These aspects should be considered because changes in concentration will occur with varying magnitudes, with the percent change in concentration calculated per the equations below:

High Extraction Drugs=$1/F$

Low Extraction Drugs=$[100/(100-MP)]$, where $MP$ is the relative contribution of major metabolic pathways to drug clearance ($CL$) as:

$$CL = CL_{ren} + CL_{1A2} + CL_{2B6} + CL_{2C9} + CL_{2C19} + CL_{2D6} + CL_{3A4} + CL_{3A5} + CL_{transporters} + CL$$

As an example, mexiletine has F=95% (low extraction ratio, high bioavailability) and 75% is cleared by CYP2D6. If the CYP2D6 enzyme is inhibited, its concentration could increase by 100/(100-MP), or 100/(100-75), roughly equivalent to a 4-fold increase in mexiletine concentration over the course of multiple doses.

In another example, simvastatin has F=5% (high extraction ratio, low bioavailability). If mechanisms underlying this low bioavailability are inhibited (CYP3A4 enzyme, transporters such as SLCO1B1, favored absorption), its concentration could increase by 1/F, or 1/0.05, roughly equivalent to a 20-fold increase in simvastatin concentration, almost immediately.

The sensitivity of the Long QT-JT Index described herein is about 86.8%, meaning that it captures roughly 87% of all medications that have been clinically shown to have effects on the QT interval and/or Torsades de Pointes. The specificity of the Long QT-JT Index is 68.1%, meaning it captures more medications as high risk (low score) than CredibleMeds classifies as being known Torsades de Pointes.

Without being limited to any one theory, there may be a few reasons for this finding. First of all, the Long QT-JT Index captures the maximum risk scenarios, where a drug is administered at a maximal dose under conditions of a drug interaction. CredibleMeds may not be taking this into account (or these medications may mostly fall under their "conditional Torsades de Pointes risk" category). Another possible explanation is that there is limited evidence published at this time to guide CredibleMeds classification strategy. Unfortunately, they are dependent on cases occurring and being published in order to classify medications with high risk.

Overall, it will be beneficial to pharmacists, prescribers, and regulatory agencies to have a pre-emptive, quantitative view of what could occur under maximal risk conditions.

Estimating Risk Factors Associated with Torsades de Pointes

In some embodiments, a number of Torsades de Pointes risk factors may be addressed when determining or otherwise estimating risk of Torsades de Pointes in a specific patient. These risk factors include female gender, age, existence of bradycardia, existence of hypokalemia, existence of hypomagnesemia, use of diuretics, use of medications that affect cardiac repolarization, existence of pharmacokinetic and pharmacodynamic interactions, existence of non-modifiable risk factors, existence of co-morbidities that may have an effect on QTc interval.

Female Gender. In a study, women accounted for 67.2% of all Torsades de Pointes cases. The sex difference in QTc interval is due to QT shortening in males after puberty, as they produce increasing levels of testosterone, rather than a lengthening of QTc in females during their reproductive years. While there is a difference in baseline QTc interval, both sexes respond similarly to given QTc-prolonging medications. Certain studies found no difference in the degree of QTc prolongation between sexes after administration of dofetilide, quinidine, ranolazine, or verapamil.

Age. A study demonstrated that women over their entire lifetime have a QT that is 5-10 milliseconds longer than men, although the difference may get smaller with age. As men age, their QT interval lengthens, with an overall difference of 10-15 milliseconds from younger males. This was also confirmed by another study, which found in a sub-group analysis that there was no difference in QTc values in either gender over the age of 50 (i.e., women only have comparably longer QTc at younger ages). Another study estimated that around age 50, men and women have similar QTc intervals again. Thus, age may be considered when assessing difference in QT due to gender.

Existence of Bradycardia. The existence of bradycardia may be person-specific, or may be induced by certain medications, e.g., beta-blockers. Use of beta-blockers may lead to underestimating the QTc interval, and thus underestimating a patient's risk of Torsades de Pointes. Another risk of bradycardia is that $I_{Kr}$ blockers prolong the repolarization time more at slower heart rates, thus compounding the risk of prolonged QTc at slower heart rates with magnified $I_{Kr}$ block. At slower heart rates, there is increased heterogeneity of repolarization, which in turn increases risk of proarrhythmias. The short-long sequence seen frequently before initiation of Torsades de Pointes also increases the heterogeneity of repolarization times, which increases the likelihood of reentrant excitation.

Existence of Hypokalemia. Low extracellular potassium (clinical hypokalemia) paradoxically prevents sufficient potassium current to flow out of the cell through $I_{Kr}$ or $I_{Ks}$, which prolongs the action potential, increasing risk for Torsades de pointes. Two proposed mechanisms include enhanced channel inactivation or exaggerated competitive blockage by $Na^+$. For example, sodium ion's typical inhibitory effect on $K^+$ channels may become more apparent when there is less competition from $K^+$. Another mechanism relates to the fact that inactivation of $K^+$ channels increases inversely with extracellular $K^+$ levels. Thus, hypokalemia will cause more $K^+$ channels to be in the inactivated state and fewer will be available to transfer $K^+$ out of the cell during the action potential. Hypokalemia may also increase drug-binding to the channel, resulting in prolonged repolarization. There are other potential mechanisms that relate hypokalemia to Torsades de Pointes, including CaM kinase activation increasing the late $Na^+$ current.

Existence of Hypomagnesemia. Magnesium is a cofactor in functioning of voltage-gated $K^+$ channels. With low $Mg^{2+}$ levels, mechanistically there may be overall less functional $I_{Kr}$ and/or $I_{Ks}$, which could prolong the action potential. Without being limited to any one theory, magnesium ion's role in increasing risk of Torsades de Pointes is due to its modulatory effects on L-type $Ca^{2+}$ channels. Generally, higher $Mg^{2+}$ levels decrease the inward $Ca^{2+}$ current, shortening phase 2 (plateau) of the action potential. With less $Mg^{2+}$, there may be less inhibition of L-type $Ca^{2+}$ channels (more functional $Ca^{2+}$ channels), which would prolong the action potential. This may be observed in practice, as intravenous $Mg^{2+}$ infusions are often successfully used to treat Torsades de Pointes.

Use of Diuretics. As described herein, electrolyte disturbances, especially hypokalemia, may predispose a patient to Torsades de Pointes. The most commonly implicated diuretics are thiazide-type and loop diuretics, with their propensity to induce hypokalemia. Indapamide has been reported to inhibit $I_{Ks}$ in addition to causing hypokalemia, and has been associated with cases of Torsades de Pointes. This blockage of $K^+$ current can be most detrimental when a coadministered agent blocks $I_{Kr}$, thus rendering both $K^+$ efflux mechanisms inadequate. While triamterene can prevent hypokalemia, it has been associated with significant block of $I_{Kr}$ and $I_{Ks}$. Thus, the use of diuretics should be considered in the overall risk picture for Torsades de Pointes.

Use of Medications that Affect Cardiac Repolarization. Class IA and Class III antiarrhythmics are used therapeutically to prevent reentrant arrhythmias. Prevention is accomplished through extending the action potential's duration—thus causing a lengthening of the refractory period—as depicted by the QT interval on a surface ECG. However, extending the QT interval too long may add risk of early afterdepoloarizations (EAD). For example, quinidine, dofetilide, and sotalol cause Torsades de Pointes in 1-5% of patients. Amiodarone routinely prolongs QT, but rarely causes Torsades de Pointes, as it also blocks L-type $Ca^{2+}$ currents and decreases the likelihood of EAD formation. Investigating other mechanisms of reducing Torsades de Pointes risk, a prospective clinical trial demonstrated that blocking the late $Na^+$ current can offset some of the QTc prolongation effects of certain medications.

Many medications that are associated with QT prolongation are implicated due to block of $I_{Kr}$. It has been shown that most drugs that block $I_{Kr}$ do so by binding to the intracellular domain. Some of the medications removed from the market due to these concerns include fenfluramine/dexfenfluramine, terfenadine, sertindole, astemizole, grepafloxacin, and cisapride. Since this time, the FDA has required thorough QT studies as part of the approval process, generally comparing the novel agent to moxifloxacin.

A specific example where a medication blocks $I_{Kr}$, but does not increase risk of Torsades de Pointes is with ranolazine. Ranolazine blocks $I_{Kr}$, but prevents experimental Torsades de Pointes potentially due to its inhibitory effect on $Na^+$ influx during the plateau (Phase 2) of the action potential. QTc prolongation due to $I_{Kr}$ effects may also be due to impaired $I_{Kr}$ component trafficking, where there is less functioning $I_{Kr}$ channels to transfer the $K^+$ channels out of the cell.

Some have tried to quantify the contribution of $I_{Kr}$ block towards the risk of QT prolongation and Torsades de Pointes. For example, a study created a quantitative medication-specific score whereby a prediction of the risk of Torsades de Pointes in clinical use may be made based on the medications propensity to block $I_{Kr}$/hERG, the effective therapeutic plasma concentration ($ETPC_{unbound}$), and electrophysiological data. In another study, various ion channel effects (Multiple Ion Channel Effects (MICE)) were viewed. After comparing the various models which included $I_{Kr}$, $I_{Na}$, and $I_{Ca}$, the study concluded that the best MICE model only required taking into account the medication's effects on $I_{Kr}$/hERG and $I_{Ca}$.

Medications that show a QT prolongation of less than 10 milliseconds generally are not a cause for concern regarding QT-related safety. For example, moxifloxacin is generally considered a positive control for producing QT prolongation, with a range of 7-10 milliseconds added to the QTc interval. However, it should be noted that while a medication administered on its own may not show evidence of QT prolongation, under conditions of drug-drug interactions, where the drugs metabolism is impaired, it may exhibit significant levels of QT prolongation, such is the case with terfenadine. Thus, even small increases in QTc upon administration of a given medication should be regarded with caution.

Existence of Pharmacokinetic and Pharmacodynamic Interactions. When metabolism is inhibited, medications will have higher concentrations throughout the body, including in the heart. A study found that roughly 35% of 249 patients experiencing Torsades de Pointes from non-cardiac drugs had a potential metabolic interaction. A patient's renal function should be considered since exemplary medications like sotalol and dofetilide are primarily eliminated by the kidneys and will have increasing concentrations in proportion to loss of kidney function. Furthermore, over-the-counter medications (OTCs) should be evaluated, including products like cimetidine and grapefruit juice, to get an accurate picture of a patient's metabolizing enzyme functionality.

Another study examined the drug-drug interaction alerts for potential risk of QTc prolongation. The study found that out of the patients who had an ECG before and after initiation of the interacting drugs, 31% had QTc prolongation to the extent that they were considered at risk for Torsades de Pointes. The average increase in QTc duration was 31 milliseconds. Giving the prescriber the ability to override the alert unfortunately did not result in subsequent recording of ECGs.

Existence of Non-Modifiable Risk Factors. Genetic risk factors have been studied by numerous groups and in a few large studies, but they have lacked specific and substantial evidence to demonstrate the role of genetics in drug-induced LQTS. The genetic variant with the most evidence for affecting drug-induced LQTS is the KCNE1 mutation D85N, which impacts $I_{Ks}$ function. The odds ratio of having this unfavorable mutation is between 9 and 12. Another study found that the KCNE1 D85N mutation predicted drug-induced LQTS with an odds ratio of 9.0 (95% confidence interval=3.5-22.9). This study looked at diLQTS cases in a European population, where population controls were all from Germany.

Existence of Co-Morbidities that May Have an Effect on QTc Interval. Patients with heart failure and left ventricular hypertrophy have an up-regulation of $Ca^{2+}$ channels and a down-regulation of $K^+$ channels, which may contribute to prolonged action potential duration, thus prolonged QT interval. In heart failure, the $I_{to}$ current is reduced and adverse effects on other mechanisms of repolarization may be more pronounced.

Another study reported that QTc prolongation was associated with a variety of clinical conditions including: congestive heart failure, ischemic cardiopathy, diabetes, renal failure, arrhythmias, hypothyroidism, and bradycardia. Patients with diabetes are at risk of Torsades de Pointes due to CV complications, nephropathy, acidosis that affects electrolyte balance, and polypharmacy. For example, PI3K signaling is decreased in mouse models of diabetes, which may alter $I_{Kr}$ trafficking to the membrane.

Situations that may precipitate electrolyte disturbances may be a preliminary indicator of risk, such as severe dieting or eating disorders, depressed/mentally ill patients, acidosis (e.g., in patients with diabetes), and renal insufficiency.

Method of Determining a Patient-Specific LQTS Score

While the medication-specific risk index may be helpful when scrutinizing a single medication, the reality is that certain patients take many medications and may have individual risk factors that may predispose or protect them from QT prolongation and Torsades de Pointes.

Figure 2:
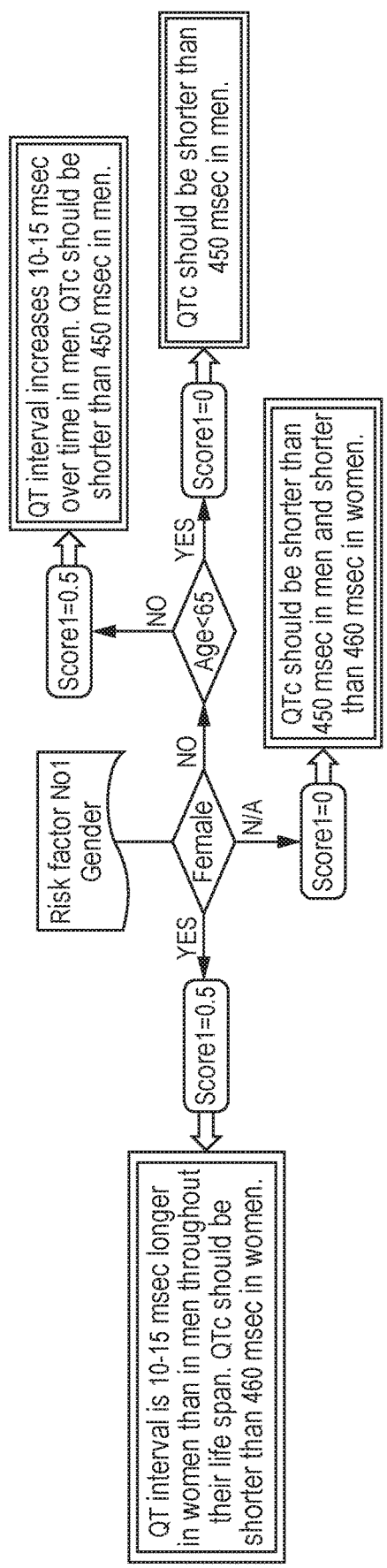
FIG. 2 is a chart illustrating the algorithm used for calculation of risk factor 1.
Figure 3:
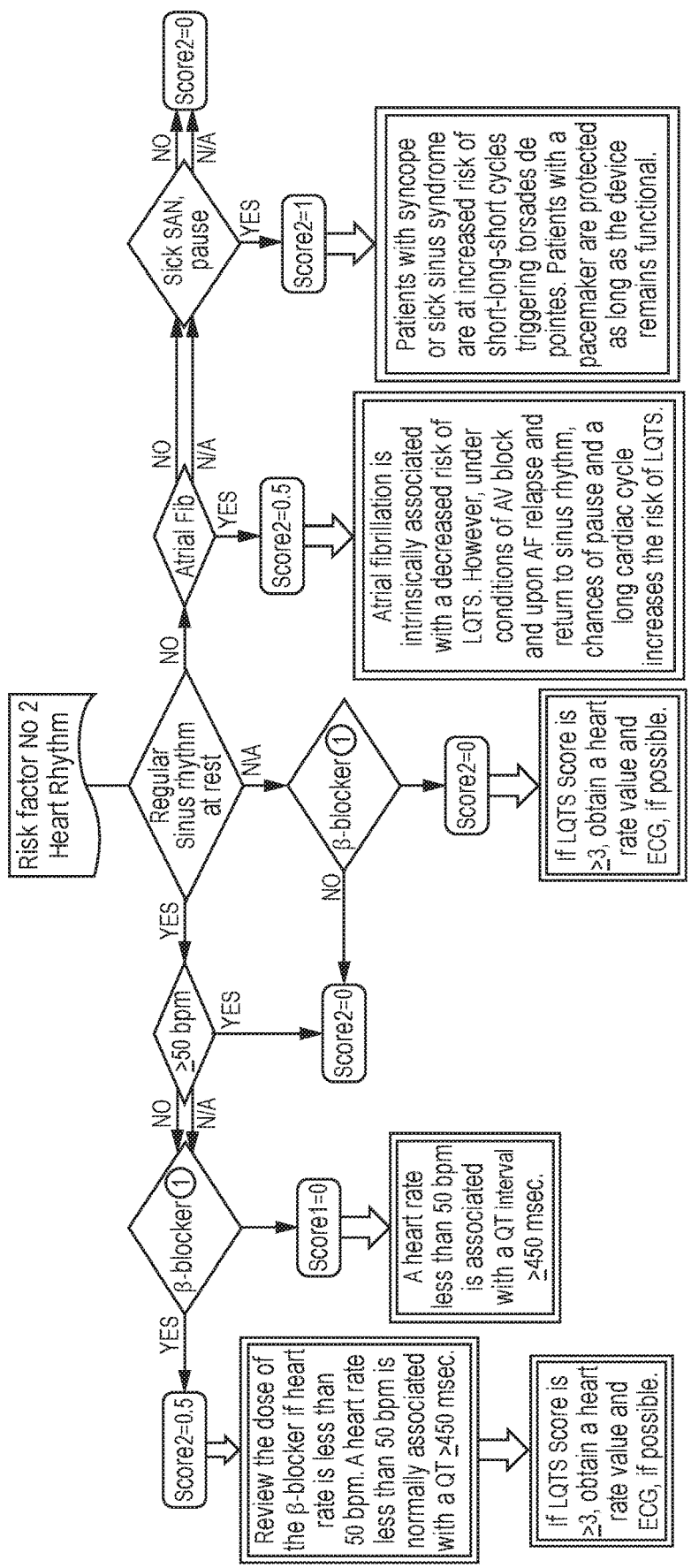
FIG. 3 is a chart illustrating the algorithm used for calculation of risk factor 2.
Figure 4:
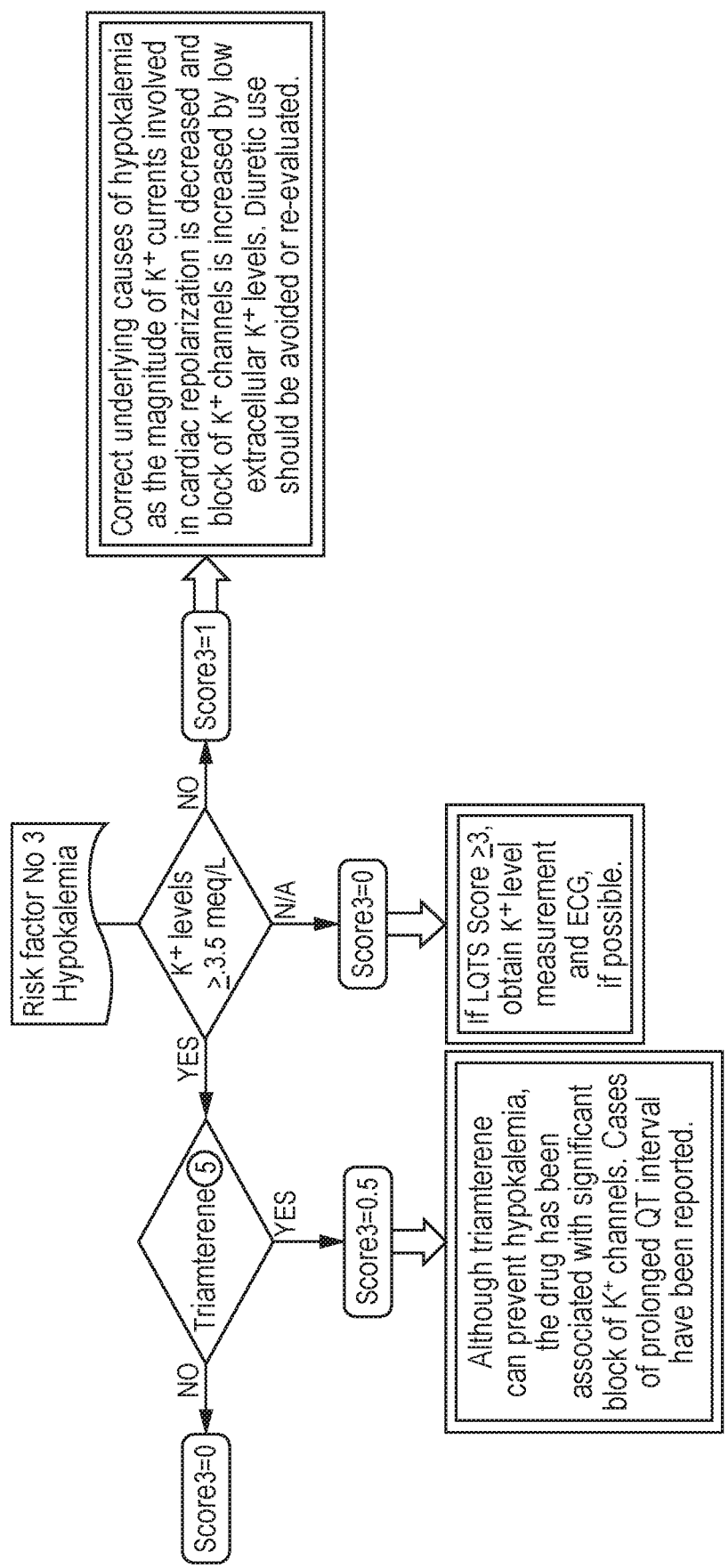
FIG. 4 is a chart illustrating the algorithm used for calculation of risk factor 3.
Figure 5:
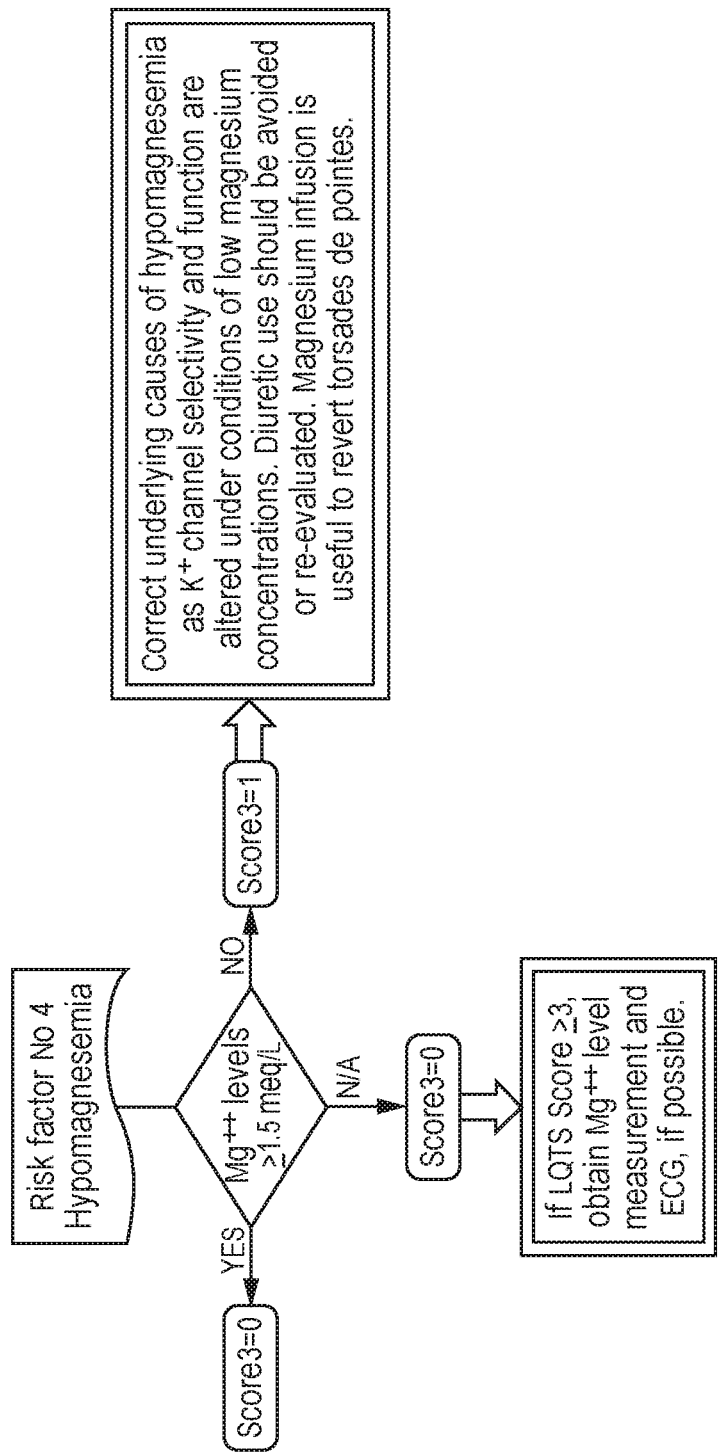
FIG. 5 is a chart illustrating the algorithm used for calculation of risk factor 4.
Figure 6:
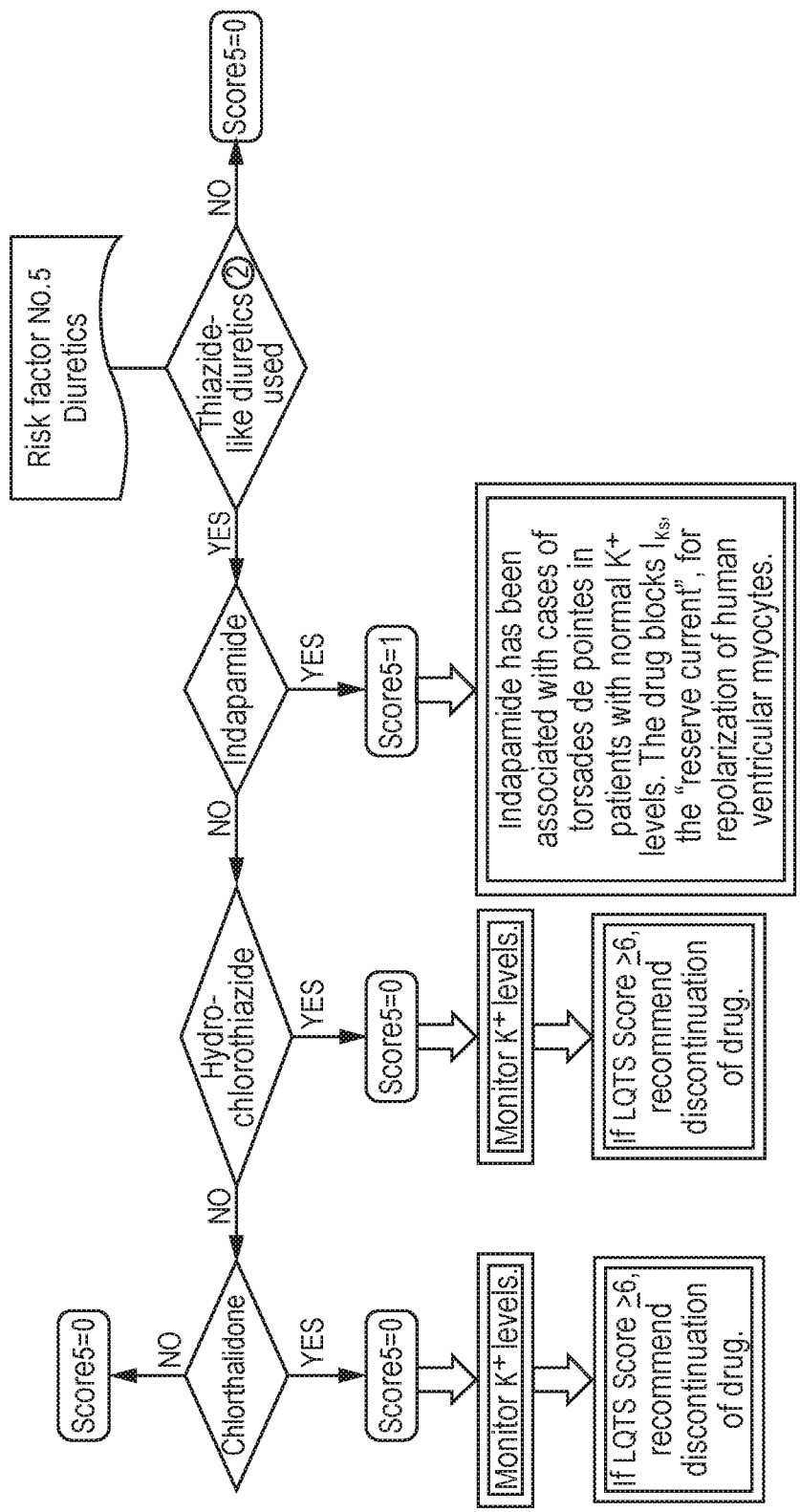
FIG. 6 is a chart illustrating the algorithm used for calculation of risk factor 5.

In some embodiments, the invention described herein includes a method for identifying a patient-specific LQTS score that is dynamic and based on a patient's current condition and medication regimen. The risk factors described herein are included based on the evidence above, and are assigned points as follows with the points determined by the associated methods illustrated in FIGS. 2 to 9 and described hereinbelow:

| Risk Factor | Description | Points Range | Point Determination Method |
|---|---|---|---|
| 1 | Male or female gender, also includes age for males | 0-0.5 | FIG. 2 |
| 2 | Heart Rhythm: sinus rhythm, Atrial Fibrillation, Sick Sinus Syndrome, Pause, Heart Rate, Beta-blocker usage | 0-1 | FIG. 3 |
| 3 | Hypokalemia (K < 3.5 mEq/L); use of triamterene | 0-1 | FIG. 4 |
| 4 | Hypomagnesemia (Mg < 1.5 mEq/L) | 0-1 | FIG. 5 |
| 5 | Diuretics | 0-1 | FIG. 6 |
| 6 | Antiarrhythmics: Class IA, Class IC, Class III; amiodarone | 0-9 | FIG. 7 |
| 7 | QT-prolonging drugs and drug interactions | 0-12 | FIG. 8 |
| 8 | QTc interval (Cut-offs: <450, <475, <500, <550, 550 + msec) | 0-10 | FIG. 9 |

In an exemplary embodiment, the points associated with risk factors 1 through 8 are added, where a sum of 10 or greater may indicate an increased risk of Torsades de Pointes.

The aforementioned model and scoring mechanism has been validated against literature cases of Torsades de Pointes. As described herein, more than 50 cases of documented Torsades de Pointes due to medication use and/or medication interactions have been identified and corresponding risk scores have been calculated based on the methods described herein. In these cases, the risk scores are generally above 10.

Point Determination Methods Associated with Each Risk Factor

As described herein, the methods for determining a patient-specific score may be based on an examination of eight risk factors. The risk factors may be represented by values or points, which are determined according to the following methods.

Although eight risk factors may be examined, in some embodiments, examination of one or more risk factors may provide evidence of a patient's risk of developing long QT syndrome or Torsades de Pointes. In some embodiments, examination of two or more risk factors may provide evidence of a patient's risk of developing long QT syndrome or Torsades de Pointes. In some embodiments, examination of three or more risk factors may provide evidence of a patient's risk of developing long QT syndrome or Torsades de Pointes. In some embodiments, examination of four or more risk factors may provide evidence of a patient's risk of developing long QT syndrome or Torsades de Pointes. In some embodiments, examination of five or more risk factors may provide evidence of a patient's risk of developing long QT syndrome or Torsades de Pointes. In some embodiments, examination of six or more risk factors may provide evidence of a patient's risk of developing long QT syndrome or Torsades de Pointes. In some embodiments, examination of seven or more risk factors may provide evidence of a patient's risk of developing long QT syndrome or Torsades de Pointes.

In some embodiments, patient symptoms and/or analyte levels (e.g., magnesium and potassium levels) may be measured from samples taken from the respective patient or recorded from the patient (e.g., by recording a patient's heart rhythm), as is generally known in the art. For example, analyte levels (e.g., levels of magnesium, potassium, diuretics, antiarrhythmics, and/or QT-prolonging drug levels) may be analyzed and/or or measured by techniques generally known in the art from a bodily fluid sample procured from the patient. In some embodiments, the bodily fluid may include, without limitation, saliva, blood, serum, or urine.

Risk Factor 1

In an embodiment, risk factor 1 may represent a value of 0 to 0.5. is the evaluation of risk factor 1 is illustrated in FIG. 2 and described below.

In an embodiment, where a patient is female, the value of risk factor 1 may be 0.5. A QT interval is 10-15 milliseconds longer in women than in men throughout their life span. Generally, QTc should be shorter than 460 milliseconds in women. Indeed, QTc should be shorter than 450 milliseconds in men and shorter than 460 milliseconds in women.

In an embodiment, where a patient is male and greater than 65 years of age, the value of risk factor 1 may be 0.5. A QT interval increases 10-15 milliseconds over time in men.

In an embodiment, where a patient is male and less than 65 years of age, the value of risk factor 1 may be 0.

Risk Factor 2

In an embodiment, risk factor 2 may represent a value of 0 to 1. The evaluation of risk factor 2 is illustrated in FIG. 3 and described below.

In an embodiment, where a patient's heart rhythm is unknown and the patient is taking a beta-blocker, the value of risk factor 2 is 0. If the patient LQTS score is greater than or equal to 3, the patient's heart rate value and ECG should be obtained, if possible.

In an embodiment, where a patient's heart rhythm is unknown and the patient not taking a beta-blocker, the value of risk factor 2 is 0.

In an embodiment, where a patient has a regular sinus rhythm at rest and a heart rate of 50 bpm or greater, the value of risk factor 2 is 0.

In an embodiment, where a patient has a regular sinus rhythm at rest, but is not taking a beta blocker, the value of risk factor 2 is 1.

In an embodiment, where a patient has a regular sinus rhythm at rest and is taking a beta blocker, the value of risk factor 2 is 0.5.

In an embodiment, where a patient has a regular sinus rhythm at rest, but does not have a heart rate of 50 bpm or greater, and is not taking a beta-blocker, the value of risk factor 2 is 1. A heart rate less than 50 bpm is associated with a QT interval of 450 milliseconds or greater.

In an embodiment, where a patient has a regular sinus rhythm at rest, but does not have a heart rate of 50 bpm or greater, and is taking a beta-blocker, the value of risk factor 2 is 0.5. The dose of the beta blocker should be reviewed if the patient's heart rate is less than 50 bpm. A heart rate less than 50 bpm is normally associated with a QT of 450 milliseconds or greater.

In an embodiment, where a patient does not have a regular sinus rhythm at rest and has atrial fibrillation, the value of risk factor 2 is 0.5. Atrial fibrillation is intrinsically associated with a decreased risk of LQTS. However, under conditions of AV block and upon AF relapse and return to sinus rhythm, chances of pause and a long cardiac cycle increase the risk of LQTS.

In an embodiment, where a patient does not have a regular sinus rhythm at rest and does not have atrial fibrillation, but has sick sinus syndrome or pause, then the value of risk factor 2 is 1. Patients with syncope or sick sinus syndrome are at increased risk of short-long-short cycles triggering Torsades de Pointes. Patients with a pacemaker are protected as long as the device remains functional.

In an embodiment, where a patient does not have a regular sinus rhythm at rest and does not have atrial fibrillation, the value of risk factor 2 is 0.

In an embodiment, where a patient does not have a regular sinus rhythm at rest and does not have sick sinus syndrome or pause, the value of risk factor 2 is 0.

In an embodiment, where a patient does not have a regular sinus rhythm at rest and does not have sick sinus syndrome or pause, the value of risk factor 2 is 0.

Risk Factor 3

In an embodiment, risk factor 3 may represent a value of 0 to 1. The evaluation of risk factor 3 is illustrated in FIG. 4 and described below.

In an embodiment, where a patient has an LQTS score of 3 or greater, the patient's potassium levels should be tested and an ECG should be performed, if possible.

In an embodiment, where a patient has a potassium level of 3.5 mEq/L or greater and is not taking triamterene, the value of risk factor 3 is 0.

In an embodiment, where a patient has a potassium level of 3.5 mEq/L or greater and is taking triamterene, the value of risk factor 3 is 0.5. Although triamterene can prevent hypokalemia, the drug has been associated with significance block of $I_{Kr}$ current. Cases of prolonged QT interval have been reported.

In an embodiment, where a patient does not have a potassium level of 3.5 mEq/L or greater, the value of risk factor 3 is 1. The underlying causes of hypokalemia should be addressed as the magnitude of potassium current involved in the cardiac repolarization is decreased and block of potassium channels is increased by low extracellular potassium levels. Diuretic use should be avoided or re-evaluated.

Risk Factor 4

In an embodiment, risk factor 4 may represent a value of 0 to 1. The evaluation of risk factor 4 is illustrated in FIG. 5 and described below.

In an embodiment, where a patient has an LQTS score of 3 or greater, the patient's magnesium levels should be tested and an ECG should be performed, if possible.

In an embodiment, where a patient has a magnesium level of 1.5 mEq/L or greater, the value of risk factor 4 is 0.

In an embodiment, where a patient does not have a magnesium level of 1.5 mEq/L or greater, the value of risk factor 4 is 1. The underlying causes of hypomagnesemia should be addressed as potassium channel selectivity and function are altered under conditions of low magnesium concentrations. Diuretic use should be avoided or re-evaluated. Magnesium infusion may be useful to reverse Torsades de Pointes.

Risk Factor 5

In an embodiment, risk factor 5 may represent a value of 0 to 1. The evaluation of risk factor 5 is illustrated in FIG. 6 and described below.

In an embodiment, where a patient is not taking a thiazide-like diuretic, the value of risk factor 5 is 0.

In an embodiment, where a patient is taking a thiazide-like diuretic and is taking indapamide, the value of risk factor 5 is 1. Indapamide has been associated with cases of Torsades de Pointes in patients with normal potassium levels. Indapamide blocks $I_{Ks}$, the "reserve current," for repolarization of human ventricular myocytes.

In an embodiment, where a patient is taking a thiazide-like diuretic and is not taking indapamide, but is taking hydro-chlorothiazide, then the value of risk factor 5 is 0. In such an instance, potassium levels in the patient should be monitored. If a patient's LQTS score is 6 or greater, hydrochlorothiazide use by the patient should be discontinued.

In an embodiment, where a patient is taking a thiazide-like diuretic and is not taking indapamide or hydro-chlorothiazide or chlorthalidone, then the value of risk factor 5 is 0.

In an embodiment, where a patient is taking a thiazide-like diuretic and is not taking indapamide or hydro-chlorothiazide, but is taking chlorthalidone, then the value of risk factor 5 is 0. In such an instance, potassium levels in the patient should be monitored. If a patient's LQTS score is 6 or greater, hydro-chlorothiazide use by the patient should be discontinued.

Risk Factor 6

Figure 7:
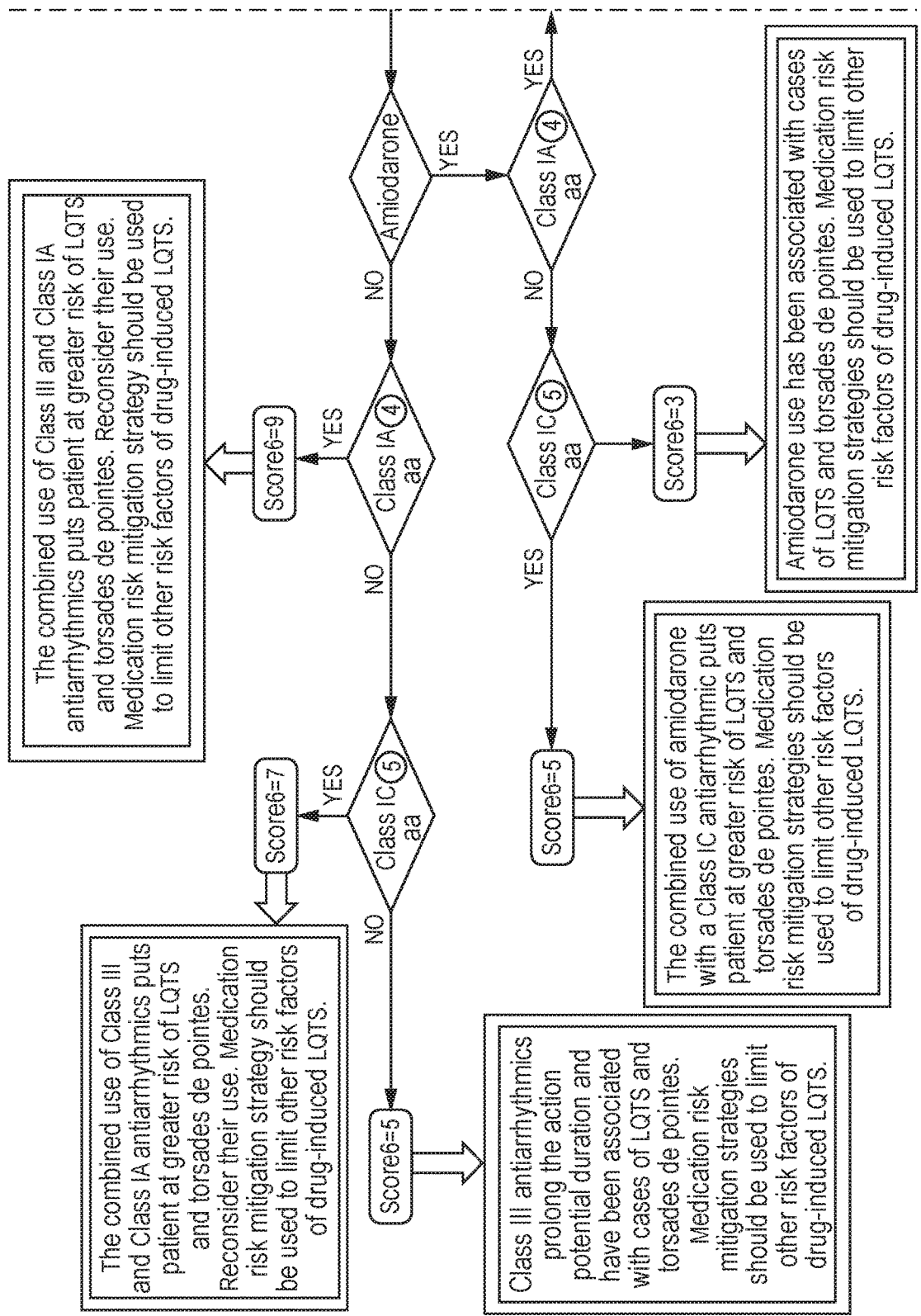
FIG. 7 is a chart illustrating the algorithm used for calculation of risk factor 6.
Figure 7:
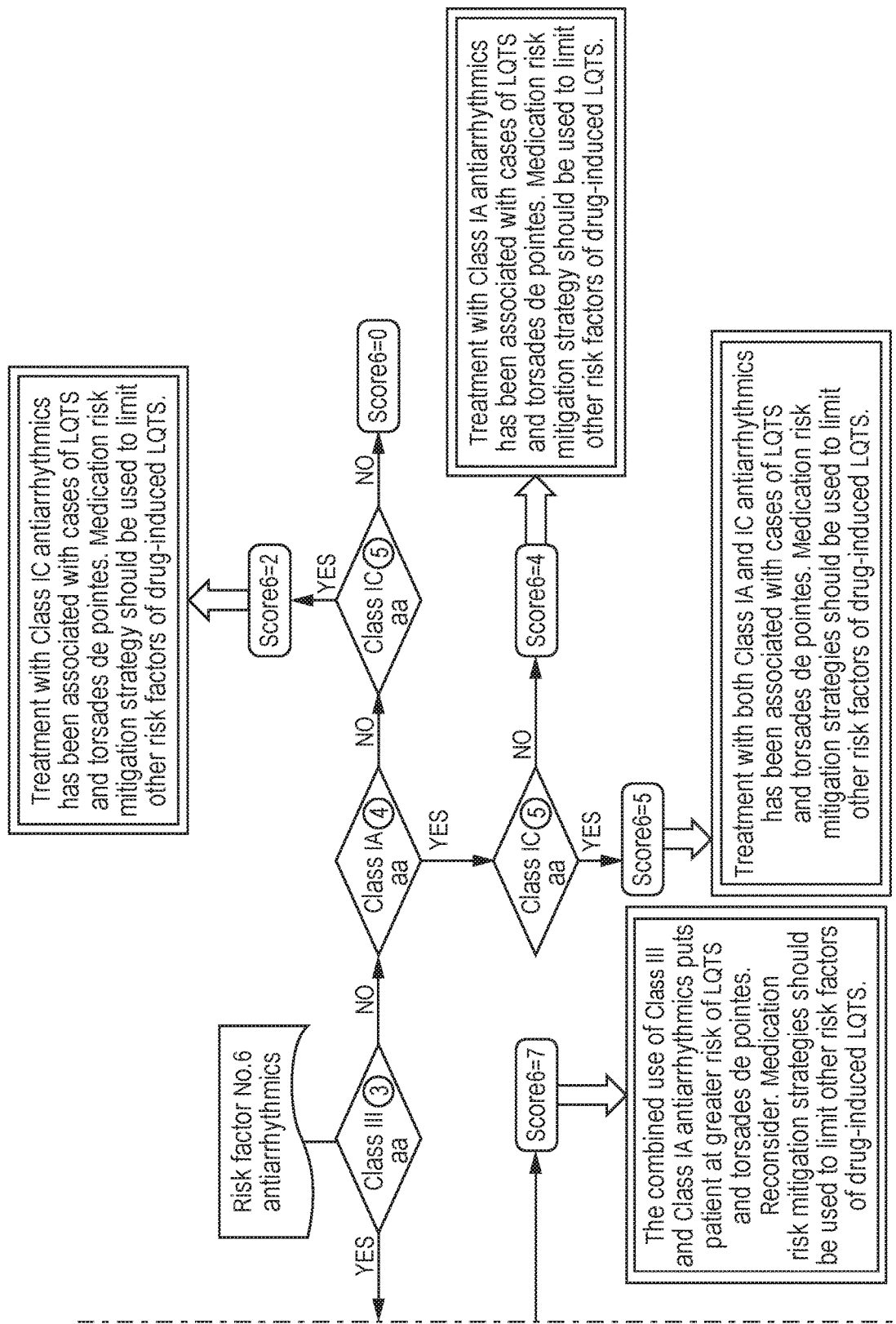

In an embodiment, risk factor 6 may represent a value of 0 to 9. The evaluation of risk factor 6 is illustrated in FIG. 7 and described below.

In an embodiment, where a patient is not taking a class III antiarrhythmic (AA), but is taking both a Class IA AA and a Class IC AA, then the value of risk factor 6 is 5. Treatment with both Class IA and IC AAs has been associated with cases of LQTS and Torsades de Pointes. Medication risk mitigation strategies should be used to limit other risk factors of drug-induced LQTS.

In an embodiment, where a patient is not taking a class III AA, but is taking a class IA AA and is not taking a class IC AA, then the value of risk factor 6 is 4. Treatment with class IA AAs has been associated with cases of LQTS and Torsades de Pointes. A medication risk mitigation strategy should be used to limit other risk factors of drug-induced LQTS.

In an embodiment, where a patient is not taking a class III AA, a class IA AA, or a class IC AA, then the value of risk factor 6 is 0.

In an embodiment, where a patient is not taking a class III AA and is not taking a class IA AA, but is taking a class IC AA, then the value of risk factor 6 is 2. Treatment with class IC AAs has been associated with cases of LQTS and Torsades de Pointes. A medication risk mitigation strategy should be used to limit other risk factors of drug-induced LQTS.

In an embodiment, where a patient is taking a class III AA and is taking amiodarone and a class IA AA, then the value of risk factor 6 is 7. The combined use of amiodarone with a class IA AA may put a patient at great risk of LQTS and Torsades de Pointes. A medication risk mitigation strategy should be used to limit other risk factors of drug-induced LQTS.

In an embodiment, where a patient is taking a class III AA and is taking amiodarone, but is not taking a class IA AA and is not taking a class IC AA, then the value of risk factor 6 is 3. Amiodarone use has been associated with cases of LQTS and Torsades de Pointes. A medication risk mitigation strategy should be used to limit other risk factors of drug-induced LQTS.

In an embodiment, where a patient is taking a class III AA and is taking amiodarone, but is not taking a class IA AA and is taking a class IC AA, then the value of risk factor 6 is 5. The combined use of amiodarone with a class IC AA may put a patient at great risk of LQTS and Torsades de Pointes. A medication risk mitigation strategy should be used to limit other risk factors of drug-induced LQTS.

In an embodiment, where a patient is taking a class III AA and is not taking amiodarone, but is taking a class IA AA, then the value of risk factor 6 is 9. The combined use of class III and class IA AAs may put a patient at great risk of LQTS and Torsades de Pointes. Their use in combination should be reconsidered. A medication risk mitigation strategy should be used to limit other factors of drug-induced LQTS.

In an embodiment, where a patient is taking a class III AA and is not taking amiodarone or a class IA AA, but is taking a class IC AA, then the value of risk factor 6 is 7. The combined use of class III and class IA AAs may put a patient at great risk of LQTS and Torsades de Pointes. Their use in combination should be reconsidered. A medication risk strategy should be used to limit other factors of drug-induced LQTS.

In an embodiment, where a patient is taking a class III AA and is not taking amiodarone, a class IA AA, or a class IC AA, then the value of risk factor 6 is 5. Class III AAs prolong the action potential duration and have been associated with cases of LQTS and Torsades de Pointes. A medication risk strategy should be used to limit other factors of drug-induced LQTS.

Risk Factor 7

In an embodiment, risk factor 7 may represent a value of 0 to 12. The evaluation of risk factor 7 is illustrated in FIG. 8 and described in the table below.

Lengthy table referenced here

US10890577-20210112-T00001

Please refer to the end of the specification for access instructions.

Risk Factor 8

Figure 9:
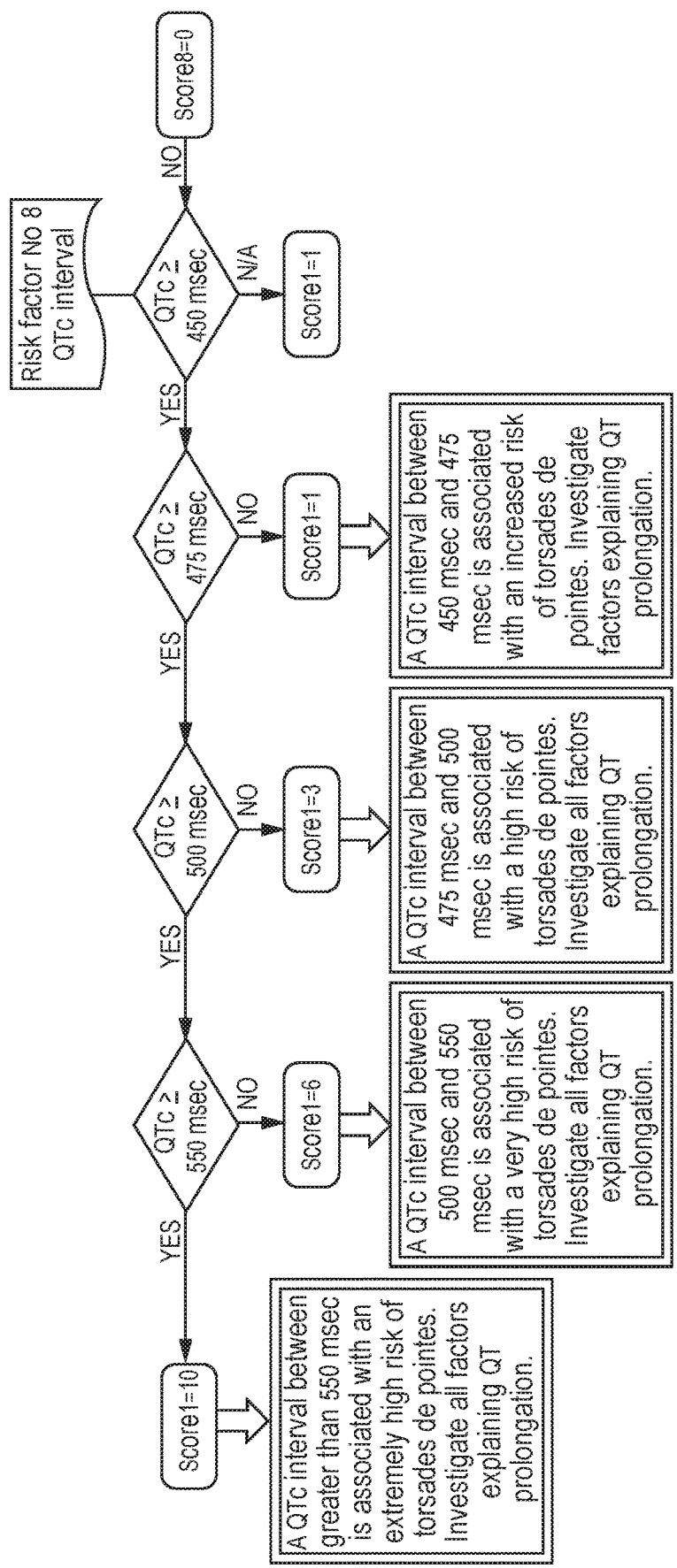
FIG. 9 is a chart illustrating the algorithm used for calculation of risk factor 8.

In an embodiment, risk factor 8 may represent a value of 0 to 10. The evaluation of risk factor 8 is illustrated in FIG. 9 and described below.

In an embodiment, where a patient does not have a QTc of greater than or equal to 450 milliseconds, the value of risk factor 8 is 0.

In an embodiment, where a patient has a QTc of between 450 milliseconds and 475 milliseconds, the value of risk factor 8 is 1. In some embodiments, a QTc interval of between 450 milliseconds and 475 milliseconds is associated with an increased risk of Torsades de Pointes. The factors explaining QT prolongation should be investigated.

In an embodiment, where a patient has a QTc of between 475 milliseconds and 500 milliseconds, the value of risk factor 8 is 3. In some embodiments, a QTc interval of between 475 milliseconds and 500 milliseconds is associated with a high risk of Torsades de Pointes. The factors explaining QT prolongation should be investigated.

In an embodiment, where a patient has a QTc of between 500 milliseconds and 550 milliseconds, the value of risk factor 8 is 6. In some embodiments, a QTc interval of between 500 milliseconds and 550 milliseconds is associated with a very high risk of Torsades de Pointes. The factors explaining QT prolongation should be investigated.

In an embodiment, where a patient has a QTc of 550 milliseconds or greater, the value of risk factor 8 is 10. In some embodiments, a QTc interval greater than 550 milliseconds is associated with an extremely high risk of Torsades de Pointes. The factors explaining QT prolongation should be investigated.

Listing of Compounds Known to Contribute to LQTS

In some embodiments, compounds that may trigger a prolongation of myocardial repolarization time or otherwise contribute to LQTS (i.e., LQTS/TdP Triggers) in a patient may include, without limitation, Albuterol, Alfuzosin, Amantadine, Amiodarone, Amitriptyline, Amphetamine, Arsenic trioxide, Astemizole, Atazanavir, Atomoxetine, Azithromycin, Bepridil, Chloral hydrate, Chloroquine, Chlorpromazine, Ciprofloxacin, Cisapride, Citalopram, Clarithromycin, Clomipramine, Clozapine, Cocaine, Desipramine, Dexmethylphenidate, Diphenhydramine, Diphenhydramine, Disopyramide, Dobutamine, Dofetilide, Dolasetron, Domperidone, Dopamine, Doxepin, Dronedarone, Droperidol, Ephedrine, Epinephrine, Erythromycin, Escitalopram, Escitalopram, Famotidine, Felbamate, Fenfluramine, Flecamide, Fluconazole, Fluoxetine, Foscarnet, Fosphenyloin, Galantamine, Gatifloxacin, Gemifloxacin, Granisetron, Halofantrine, Haloperidol, Ibutilide, Imipramine, Indapamide, Isoproterenol, Isoproterenol, Isradipine, Itraconazole, Ketoconazole, Lapatinib, Lapatinib, Levalbuterol, Levofloxacin, Levomethadyl, Lisdexamfetamine, Lithium, Mesoridazine, Metaproterenol, Methadone, Methylphenidate, Midodrine, Moexipril/HCTZ, Moxifloxacin, Nicardipine, Nilotinib, Norepinephrine, Nortriptyline, Octreotide, Ofloxacin, Ondansetron, Oxytocin, Paliperidone, Paroxetine, Pentamidine, Perflutren lipid microspheres, Phentermine, Phenylephrine, Phenylpropanolamine, Pimozide, Probucol, Procainamide, Protriptyline, Pseudoephedrine, Quetiapine, Quinidine, Ranolazine, Risperidone, Ritodrine, Ritonavir, Roxithromycin, Salmeterol, Sertindole, Sertraline, Sibutramine, Solifenacin, Sotalol, Sparfloxacin, Sunitinib, Tacrolimus, Tamoxifen, Telithromycin, Terbutaline, Terfenadine, Thioridazine, Tizanidine, Tolterodine, Trazodone, Trimethoprim-Sulfa, Trimipramine, Vandetanib, Vardenafil, Venlafaxine, Voriconazole, or Ziprasidone and the pharmaceutically acceptable salts thereof.

In some embodiments, LQTS/TdP Triggers may include, without limitation, class IA antiarrhythmics, class IC antiarrhythmics, or class III antiarrhythmics and the pharmaceutically acceptable salts thereof.

Listing of Compounds Used in the Treatment of LQTS

In some embodiments, one or more compounds may be provided for the treatment of Long QT Syndrome and/or Torsades de Pointes (i.e., LQTS Medicaments or TdP Medicaments) upon a determination that a patient is identified as having a high risk of Long QT Syndrome and/or Torsades de Pointes. In some embodiments, such one or more compounds may include, but are not limited to potassium and/or magnesium.

In some embodiments, such one or more compounds used in the treatment of Long QT Syndrome and/or Torsades de Pointes may include potassium such as in the form of a potassium salt (e.g., KCl).

In some embodiments, such one or more compounds used in the treatment of Long QT Syndrome and/or Torsades de Pointes may include magnesium such as in the form of a magnesium salt (e.g., MgSO$_4$). For example, a magnesium sulfate infusion may be administered as an IV bolus (e.g., a 2 gram bolus), which may be followed by an IV infusion of magnesium at a rate of 2-4 mg per minute.

In some embodiments, such one or more compounds used in the treatment of Long QT Syndrome and/or Torsades de Pointes may include a compound described in U.S. Pat. Nos. 8,183,284, 8,658,358, 8,753,674, 8,987,262, 9,126,989, 9,447,027, or 9,597,302, the entirety of which are incorporated herein by reference.

Pharmaceutical Compositions

In some embodiments, the invention includes a pharmaceutical composition for use in the treatment of the diseases and conditions described herein. In some embodiments, the invention includes a pharmaceutical composition comprising one or more LQTS/TdP Triggers, or a pharmaceutically acceptable salt thereof. In some embodiments, the invention includes one or more LQTS Medicaments, or a pharmaceutically acceptable salt thereof.

Where desired, the pharmaceutical compositions contain a pharmaceutically acceptable salt and/or coordination complex of one or more of the active ingredients. Typically, the pharmaceutical compositions also comprise one or more pharmaceutically acceptable excipients, carriers, including inert solid diluents and fillers, diluents, including sterile aqueous solution and various organic solvents, permeation enhancers, solubilizers and adjuvants.

The pharmaceutical compositions described above that include LQTS Medicaments are preferably for use in the treatment of the LQTS and/or Torsades de Pointes.

Where desired, other active pharmaceutical ingredient(s) may be mixed into a preparation or two or more components of the combination may be formulated into separate preparations for use in combination separately or at the same time. A kit containing the components of the combination, formulated into separate preparations for said use, in also provided by the invention.

In some embodiments, the concentration of any LQTS/TdP Trigger or LQTS Medicament provided in the pharmaceutical compositions of the invention is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of any LQTS/TdP Trigger or LQTS Medicament provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of any LQTS/TdP Trigger or LQTS Medicament provided in the pharmaceutical compositions is independently in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of any LQTS/TdP Trigger or LQTS Medicament provided in the pharmaceutical compositions is independently in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of any LQTS/TdP Trigger or LQTS Medicament provided in the pharmaceutical compositions is independently equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of any LQTS/TdP Trigger or LQTS Medicament provided in the pharmaceutical compositions is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5 g, 0.4 g, 4.5 g, 5 g, 5.5 g, 6 g, 6.5 g, 7 g, 7.5 g, 8 g, 8.5 g, 9 g, 9.5 g, or 10 g.

Each of the LQTS/TdP Triggers or LQTS Medicaments according to the invention is effective over a wide dosage range. For example, in the treatment of adult humans, dosages independently ranging from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting pharmaceutical compositions and methods for preparing the same.

Pharmaceutical Compositions for Oral Administration

In certain embodiments, the invention provides a pharmaceutical composition for oral administration containing one or more LQTS/TdP Triggers or LQTS Medicaments, and a pharmaceutical excipient suitable for administration.

In certain embodiments, the invention provides a solid pharmaceutical composition for oral administration containing: (i) an effective amount of one or more LQTS/TdP Triggers or LQTS Medicaments and (ii) a pharmaceutical excipient suitable for administration.

In some embodiments, the pharmaceutical composition may be a liquid pharmaceutical composition suitable for oral consumption.

Pharmaceutical compositions of the invention suitable for oral administration can be presented as discrete dosage forms, such as capsules, sachets, tablets, liquids, or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the one or more LQTS/TdP Triggers or LQTS Medicaments as active ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10-oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In certain embodiments, the invention provides a pharmaceutical composition for injection containing the combination of one or more LQTS/TdP Triggers or LQTS Medicaments, and a pharmaceutical excipient suitable for injection. Components and amounts of agents in the compositions are as described herein.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating the combination of the one or more LQTS/TdP Triggers or LQTS Medicaments in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In certain embodiments, the invention provides a pharmaceutical composition for transdermal delivery containing the combination of one or more LQTS/TdP Triggers or LQTS Medicaments, and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of the one or more LQTS/TdP Triggers or LQTS Medicaments in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Other Pharmaceutical Compositions

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of the combination of one or more LQTS/TdP Triggers or LQTS Medicaments or pharmaceutical compositions of these compounds can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The combination of compounds can also be administered intraadiposally or intrathecally.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. The combination of the one or more LQTS/TdP Triggers or LQTS Medicaments may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include each of the one or more LQTS/TdP Triggers or LQTS Medicaments, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In some embodiments, the one or more LQTS/TdP Triggers or LQTS Medicaments and another active pharmaceutical ingredient are provided as separate compositions in separate containers within the kit. In some embodiments, the one or more LQTS/TdP Triggers or LQTS Medicaments and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Dosages and Dosing Regimens

The amounts of the one or more LQTS/TdP Triggers or LQTS Medicaments administered will be dependent on the human or mammal being treated, the severity of the disorder or condition, the rate of administration, the disposition of the compounds and the discretion of the prescribing physician. However, an effective dosage of each is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of one or more LQTS/TdP Triggers or LQTS Medicaments may be provided in units of mg/kg of body mass or in mg/m$^2$ of body surface area.

Administration of the active pharmaceutical ingredients of the invention may continue as long as necessary. In some embodiments, the combination of one or more LQTS/TdP Triggers or LQTS Medicaments is administered for more than 1, 2, 3, 4, 5, 6, 7, 14, or 28 days. In some embodiments, the combination of one or more LQTS/TdP Triggers or LQTS Medicaments is administered for less than 28, 14, 7, 6, 5, 4, 3, 2, or 1 day. In some embodiments, the combination of one or more LQTS/TdP Triggers or LQTS Medicaments is administered chronically on an ongoing basis—e.g., for the treatment of chronic effects. In another embodiment the administration of the combination of the one or more LQTS/TdP Triggers or LQTS Medicaments continues for less than about 7 days. In yet another embodiment the administration continues for more than about 6, 10, 14, 28 days, two months, six months, or one year. In some cases, continuous dosing is achieved and maintained as long as necessary.

In some embodiments, an effective dosage of a LQTS/TdP Trigger or LQTS Medicament disclosed herein is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of a LQTS/TdP Trigger or LQTS Medicament disclosed herein is about 25 mg, about 50 mg, about 75 mg, about 100 mg, about 125 mg, about 150 mg, about 175 mg, about 200 mg, about 225 mg, or about 250 mg.

In some embodiments, an effective dosage of a LQTS/TdP Trigger or LQTS Medicament disclosed herein is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a LQTS/TdP Trigger or LQTS Medicament disclosed herein is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some instances, dosage levels below the lower limit of the aforesaid ranges may be more than adequate, while in other cases still larger doses may be employed without causing any harmful side effect—e.g., by dividing such larger doses into several small doses for administration throughout the day.

An effective amount of the combination of one or more LQTS/TdP Triggers or LQTS Medicaments may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

Method of Treating a Patient Susceptible to LQTS

In an embodiment, the invention includes a method of treating patients who are susceptible or at risk of developing long QT syndrome or Torsades de Pointes. In some embodiments, the method includes the step of determining whether the patient has an increased risk of developing long QT syndrome or Torsades de Pointes due to a patient-specific score of greater than 10. In some embodiments, where the patient specific score is greater than 10, the method may include the step of administering a pharmaceutical composition to the patient comprising a therapeutically effective amount of an LQTS Medicament, and a pharmaceutically acceptable carrier.

In an embodiment, the invention includes a method of treating patients who may be susceptible or at risk of developing long QT syndrome or Torsades de Pointes. In some embodiments, the method includes the step of determining whether the patient has an increased risk of developing long QT syndrome or Torsades de Pointes due to a patient-specific score of greater than 10. In some embodiments, where the patient specific score is greater than 10, the method may include the step of administering a pharmaceutical composition to the patient comprising a therapeutically effective amount of an LQTS Medicament, and a pharmaceutically acceptable carrier. In some embodiments, where the patient specific score is not greater than 10, the method may include the step of step of administering a pharmaceutical composition to the patient comprising a therapeutically effective amount of an LQTS/TdP Trigger, and a pharmaceutically acceptable carrier.

In an embodiment, the invention includes a method of treating patients having an increased risk of developing long QT syndrome or Torsades de Pointes due to a patient-specific score of greater than 10. In some embodiments, the method may include the administration of a therapeutically effective amount of an LQTS Medicament, as described herein.

In an embodiment, the invention includes a method of treating a patient with an LQTS/TdP Trigger, which is determined to increase the risk of long QT syndrome or Torsades de Pointes. In some embodiments, the method may include the step of confirming that the patient does not have an increased risk of developing long QT syndrome or Torsades de Pointes due to a patient-specific score of greater than 10. In some embodiments, the method may include the step of administering a pharmaceutical composition to the patient including a therapeutically effective amount of the LQTS/TdP Trigger, and a pharmaceutically acceptable carrier.

In an embodiment, the invention may include a method of treating a patient with an LQTS/TdP Trigger, which is determined to increase the risk of long QT syndrome or Torsades de Pointes, which may include the step of administering a pharmaceutical composition to the patient including a therapeutically effective amount of the LQTS/TdP Trigger, and a pharmaceutically acceptable carrier. In some embodiments, the method may include the step of determining whether the patient has an increased risk of developing long QT syndrome or Torsades de Pointes due a patient-specific score that is indicative of an increased risk of developing long QT syndrome or Torsades de Pointes. In some embodiments, the patient-specific score that is indicative of an increased risk of developing long QT syndrome or Torsades de Pointes is greater than 10. In some embodiments, the method may further include halting treatment of the patient with the pharmaceutical composition. In some embodiments, the method may further include the administration of an additional pharmaceutical composition to the patient that does not include the LQTS/TdP Trigger. In some embodiments, the additional pharmaceutical composition includes an additional compound that has a drug-specific index that is not less than 15. In some embodiments, the additional pharmaceutical composition includes an additional compound that is an LQTS Medicament.

In some embodiments of the methods described herein, such methods may include the step inserting a pacing catheter in the right ventricular chamber of the patient, wherein the pacing catheter may be attached to an external pacemaker.

In some embodiments of the methods described herein, such methods may include the step of providing an Implantable Cardioverter Defribillator (ICD) at the patient or implanted in the patient to pace the hearth rhythm and prevent bradycardia, which may lead to an increased QTc interval.

While preferred embodiments of the invention are shown and described herein, such embodiments are provided by way of example only and are not intended to otherwise limit the scope of the invention. Various alternatives to the described embodiments of the invention may be employed in practicing the invention.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—Validation of Drug-Specific LQTS Index with Terfenadine

Terfenadine is a non-sedating H1-antagonist that has been associated with several cases of QT prolongation and Torsades de Pointes, starting in the 90's. The drug was removed from the US market in January of 1997. Using pharmacological characteristics of terfenadine, the LQTS Index is calculated, which may be described as the sum of K1+K2+K3−K4 (where K4 is either a 0 or a subtraction of 5 from the sum of K1, K2, and K3).

Calculating LQTS index for terfenadine yields the following:

$$K1=(0.016*1000)/(3.18*((100-97)/100)*(381.6/127.20)*(100/5))$$

K2=0

K3=0

K4=0

The computed LQTS index for terfenadine is therefore 2.795. This value is lower than the determined threshold for risk (15) and exemplifies a drug with high risk of QT prolongation and drug-induced Torsade de Pointes.

Example 2—Validation of Long QT-JT Index for 155 Drugs

A drug specific LQTS index was calculated for 155 drugs as demonstrated in Example 1. The Z-score distribution of values obtained for each of these drugs was then plotted. Drugs were also categorized based on CredibleMeds characterization (www.crediblemeds.org) to either High risk, Conditional risk, Low risk, or Undetermined risk. A specificity and sensitivity analysis performed demonstrated that a threshold value 15 was associated with maximum specificity and maximum sensitivity (see FIG. 1).

Example 3—Evaluation of a Patient-Specific LQTS Score in an Exemplary Female Patient An exemplary female patient with atrial fibrillation was being treated with sotalol (rhythm control of atrial fibrillation) and ciprofloxacin (urinary tract infection). Her potassium level was at 3.1 meq/L and she had a measured QTc at 560 msec.

FIG. 10 illustrates an exemplary data input screen for calculating a patient-specific LQTS score and the results of such score are shown below where the patient in FIG. 10 has an LQTS Score of 19.

LQTS Analysis Result: A total LQTS Score of 19 was estimated for this patient based on available information. This represents a precarious condition, which requires immediate attention. However, the Total LQTS Score could be higher if all risk factors were taken into consideration. The missing risk factors are: (1) magnesium level; and (2) heart rate.

Risk Factor 1: 0.5. QT interval is 10-15 milliseconds longer in women than in men throughout their life span. QTc should be shorter than 450 milliseconds in women.

Risk Factor 2: 0.5. Atrial fibrillation is intrinsically associated with a decreased risk of LQTS. However, under conditions of AV block and upon AF relapse and return to sinus rhythm, chances of pause and a long cardiac cycle increase the risk of LQTS.

Risk Factor 3: 1. Underlying causes of hypokalemia should be corrected as the magnitude of potassium currents involved in cardiac repolarization is decreased and block of potassium channels is increased by low extracellular potassium levels. Diuretic use should be avoided or re-evaluated.

Risk Factor 4: 0. Since the LQTS Score is greater than or equal to 4.5, magnesium levels should be obtained, if possible.

Risk Factor 5: 0.

Risk Factor 6: 5. Class III antiarrhythmics prolong the action potential duration and have been associated with cases of LQTS and Torsades de Pointes. Medication risk mitigation strategies should be used to limit other risk factors of drug induced LQTS.

Risk Factor 7: 2. Ciprofloxacin and Sotalol have been associated with a prolongation of the QT interval and Torsades de Pointes. Other risk factors of drug-induced LQTS should be limited.

Risk Factor 8: 10. A QTc interval greater than 550 milliseconds is associated with an extremely high risk of Torsades de Pointes. All factors explaining QT prolongation should be investigated.

LENGTHY TABLES

The patent contains a lengthy table section. A copy of the table is available in electronic form from the USPTO web site (https://seqdata.uspto.gov/?pageRequest=docDetail&DocID=US10890577B2). An electronic copy of the table will also be available from the USPTO upon request and payment of the fee set forth in 37 CFR 1.19(b)(3).

It is claimed:

1. An ex vivo method for determining whether a medication is associated with an increased risk of long QT syndrome or Torsades de Pointes in combination with at least one other drug by determining a drug-specific index for the medication, the method comprising the steps of:
   (i) calculating a first index variable by determining:
      an $IC_{50}$ value for block of one or more of $I_{Kr}$ and $I_{Ks}$
      a Cmax of the medication at a test dose,
      a daily dose amount of the medication,
      a protein binding value for the medication at a target protein,
      a drug-drug interaction coefficient (DDIC) for the medication, and
      calculating a value for the first index variable based on the following equation:

$$\frac{(IC_{50} \text{ of } I_{Kr} \text{ or } I_{Ks} \text{ block}) \times 1000}{(Cmax \text{ Dose Test}) \times \left(\frac{100 - \text{Protein Binding \%}}{100}\right) \times \left(\frac{\text{Daily Dose Administered}(\mu moles)}{\text{Dose Test}(\mu mole) \times DDIC}\right)};$$

(ii) calculating a second index variable by determining:
      an $IC_{50}$ value for block of CaV1.2 current,
      the $IC_{50}$ value for block of one or more of $I_{Kr}$ and $I_{Ks}$, and
      calculating a value for the second index variable based on the following equation:

$$\frac{IC_{50} \text{ for block of } CaV1.2 \text{ current}}{IC_{50} \text{ for lock of } I_{Kr} \text{ or } I_{Ks}};$$

(iii) calculating a third index variable by determining:
      an $IC_{50}$ value for block of NaV1.5 current,
      the $IC_{50}$ value for block of one or more of $I_{Kr}$ and $I_{Ks}$, and
      calculating a value for the third index variable based on the following equation:

$$\frac{IC_{50} \text{ for block of } NaV1.5 \text{ current}}{IC_{50} \text{ for block of } I_{Kr} \text{ or } I_{Ks}};$$

(iv) calculating a value for a fourth index variable based on whether the medication is an inhibitor of hERG trafficking; and
   (v) combining the values for the first, second, third, and fourth index variables to provide the drug-specific index, wherein a drug-specific index of less than a predetermined threshold value is indicative of an increased risk of long QT syndrome or Torsades de Pointes for the medication in combination with the at least one other drug.

2. An ex vivo method for determining whether a patient undergoing treatment with one or more medications has an increased risk of long QT syndrome or Torsades de Pointes by determining a patient-specific score, the method comprising:
   one or more steps (a)-(g):
   (a) determining a risk variable having a value between 0 and 0.5 based on the patient's gender and age;
   (b) determining a risk variable having a value between 0 and 1 based on a measurement of the patient's heart rhythm, the measurement comprising detecting one or more of sinus rhythm, atrial fibrillation, sick sinus syndrome, pause, and heart rate;
   (c) determining a risk variable having a value between 0 and 1 based on a detected potassium level in the patient;
   (d) determining a risk variable having a value between 0 and 1 based on a detected magnesium level in the patient;
   (e) determining a risk variable having a value between 0 and 1 based on a detected presence of one or more diuretics in the patient;
   (f) determining a risk variable having a value between 0 and 9 based on a detected presence of one or more antiarrhythmics in the patient:
   (g) determining a risk variable having a value between 0 and 12 based on calculating a drug-specific index for the one or more medications in the patient's treatment regimen, including the patient's use of OT-prolonging drugs and/or a presence of drug-drug interactions, and
   (f) determining a risk variable having a value between 0 and 10 based on the patient's QT interval;
   the method further comprising combining the determined risk variables from the one or more of steps (a)-(g) to obtain a patient-specific score, wherein a patient-specific score exceeding a predetermined threshold value is indicative that the patient has an increased risk of long QT syndrome or Torsades de Pointes.

3. The ex vivo method of claim 1, further comprising: treating a patient with the medication determined to have the drug-specific index indicative of an increased risk of long QT syndrome or Torsades de Pointes in combination with the at least one other drug, wherein the treatment of the patient comprises the steps of:
   administering a pharmaceutical composition to the patient comprising a therapeutically effective amount of the medication or a pharmaceutically acceptable salt thereof, and a pharmaceutically acceptable carrier;
   determining whether the patient has an increased risk of developing long QT syndrome or Torsades de Pointes due to a patient-specific score that is indicative of an increased risk of developing long QT syndrome or Torsades de Pointes; and
   halting treatment of the patient with the pharmaceutical composition.

4. The ex vivo method of claim 3, further comprising the step of administering an additional pharmaceutical composition to the patient that does not include the medication.

5. The ex vivo method of claim 1, wherein the predetermined threshold value has a value of 15.

6. The ex vivo method of claim 1, wherein the value of the second index variable is derived such that:
- a value of less than 1 yielded by the equation for calculating the second index variable yields a second index variable value of 10;
- a value of between 1 to less than 5 yielded by the equation for calculating the second index variable yields a second index variable value of 5; and
- a value of between 5 and less than 10 yielded by the equation for calculating the second index variable yields a second index variable value of 2.

7. The ex vivo method of claim 1, wherein the value of the third index variable is derived such that:
- a value of less than 1 yielded by the equation for calculating the third index variable yields a third index variable value of 10;
- a value of between 1 to less than 5 yielded by the equation for calculating the third index variable yields a third index variable value of 5; and
- a value of between 5 and less than 10 yielded by the equation for calculating the third index variable yields a third index variable value of 2.

8. The ex vivo method of claim 1, wherein the value of the fourth index variable is −5 if the medication is an inhibitor of hERG trafficking, and the fourth index variable is 0 if the medication is not an inhibitor of hERG trafficking.

9. The ex vivo method of claim 2, wherein the predetermined threshold value has a value of 10.

* * * * *